US011331384B2

(12) United States Patent
Anderson

(10) Patent No.: US 11,331,384 B2
(45) Date of Patent: May 17, 2022

(54) COMPUTATIONAL ALGORITHM FOR UNIVERSAL VACCINE SELECTION

(71) Applicant: University of Rochester, Rochester, NY (US)

(72) Inventor: Christopher S. Anderson, Pittsford, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 16/869,901

(22) Filed: May 8, 2020

(65) Prior Publication Data

US 2020/0353067 A1 Nov. 12, 2020

Related U.S. Application Data

(60) Provisional application No. 62/925,935, filed on Oct. 25, 2019, provisional application No. 62/845,030, filed on May 8, 2019.

(51) Int. Cl.
*A61K 39/12* (2006.01)
*A61K 39/00* (2006.01)

(52) U.S. Cl.
CPC ........ *A61K 39/12* (2013.01); *A61K 2039/545* (2013.01); *A61K 2039/55511* (2013.01)

(58) Field of Classification Search
None
See application file for complete search history.

(56) References Cited

U.S. PATENT DOCUMENTS

2020/0353067 A1* 11/2020 Anderson ............... A61P 31/14
2020/0399311 A1* 12/2020 Jain ........................... A61P 9/10

FOREIGN PATENT DOCUMENTS

WO WO 2008/061243 * 5/2008
WO WO 2016/160166 * 10/2016

OTHER PUBLICATIONS

Alignment of SEQ 1 with Geneseq db access No. ARV49321 by Smith et al in WO2008061243 May 2008.*
Alignment of SEQ 3 with Geneseq db access No. ARV49321 by Smith et al in WO2008061243 May 2008.*
Alignment of SEQ 2 with Geneseq db access No. BDG33984 by Khurana et al. in WO2016160166 on Oct. 2016.*
Choi et al. (Viral Immunology. 2012; 25 (3): 193-203).*
Anderson, C. S. et al., "Antigenic Cartography of H1N1 Influenza Viruses Using Sequence-Based Antigenic Distance Calculation" BMC Bioninformatics (2018); vol. 19:51; 11 pgs.
Anderson, C. S.et al., "Natural and Directed Antigenic Drift of the H1 Influenza Virus Hemagglutinin Stalk Doman"; Scientific Reports (2018); vol. 8:276; 20 pgs.
Anderson, C.S. et al., "Novel Sequence-Based Mapping of Recently Emergering H5NX Influenza Viruses Reveals Pandemic Vaccine Candidates"; PLOS-One (2016); 14 pgs.

* cited by examiner

*Primary Examiner* — Shanon A. Foley
(74) *Attorney, Agent, or Firm* — Fox Rothschild LLP

(57) ABSTRACT

This invention relates to methods to determine vaccine candidate strains that can be used to induce broadly cross-reactive immunity against pathogens, related vaccines, and related methods.

14 Claims, 16 Drawing Sheets

Specification includes a Sequence Listing.

Figures 9A, 9B, and 9C

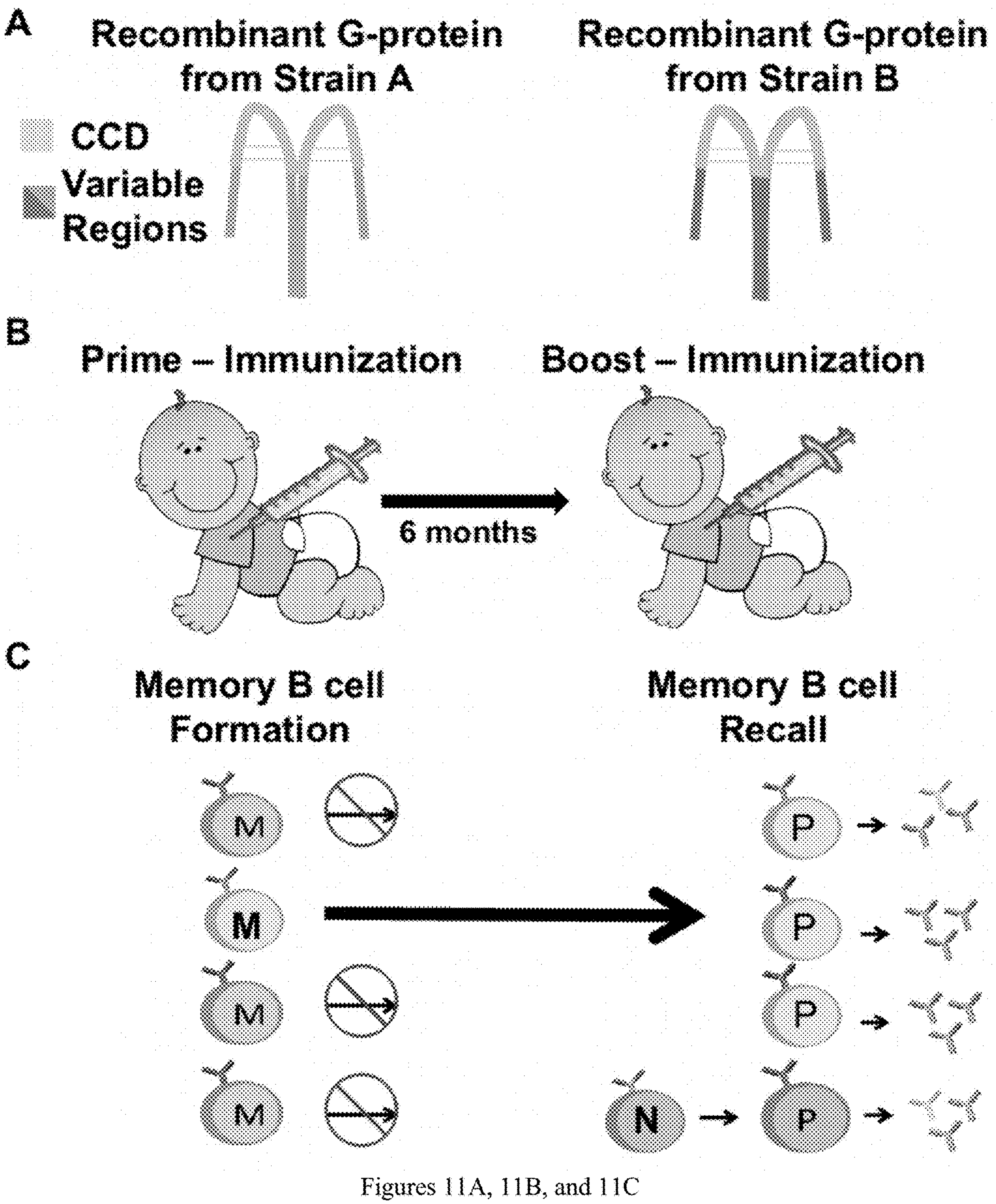
Figures 11A, 11B, and 11C

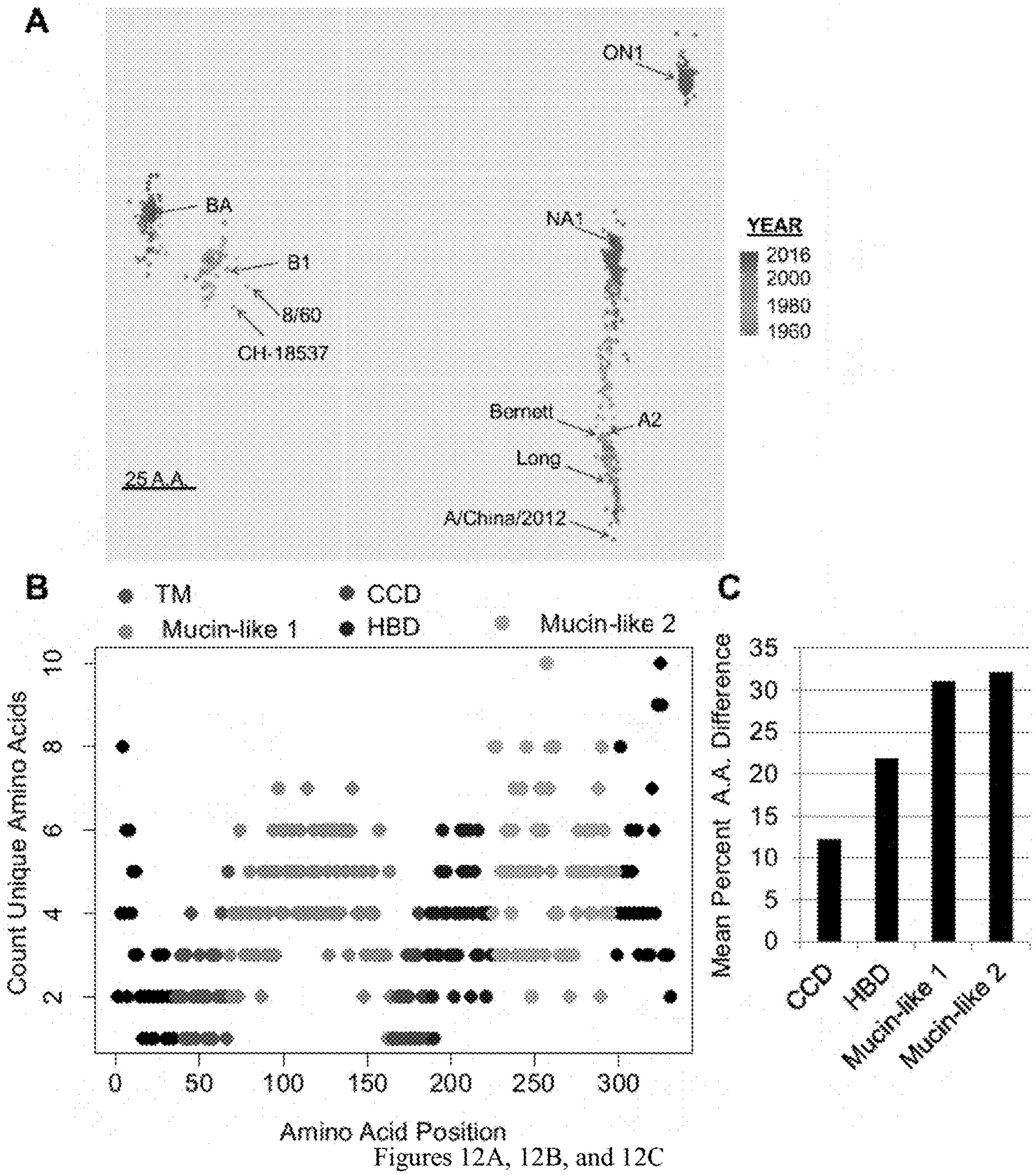
Figures 12A, 12B, and 12C

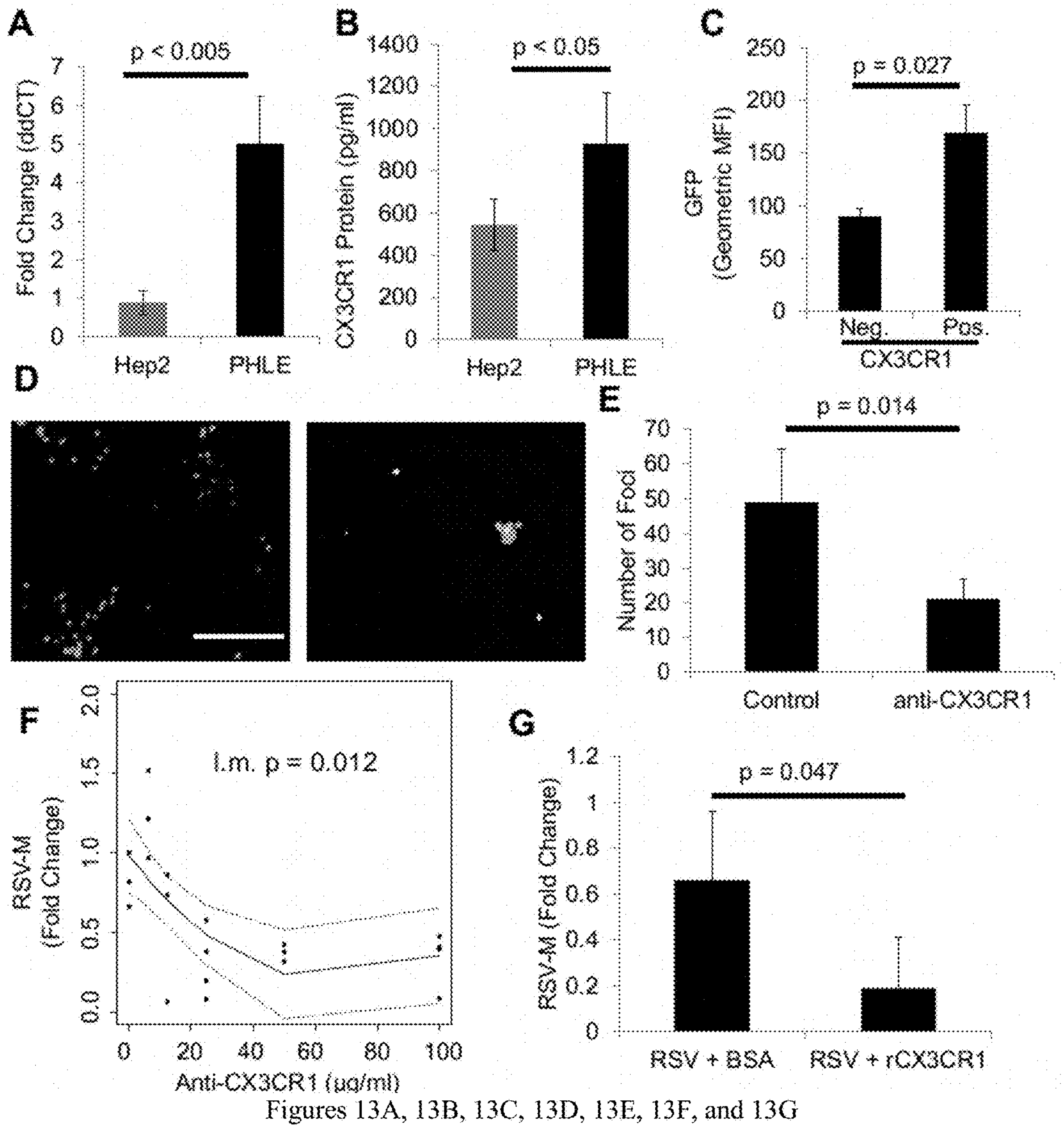
Figures 13A, 13B, 13C, 13D, 13E, 13F, and 13G

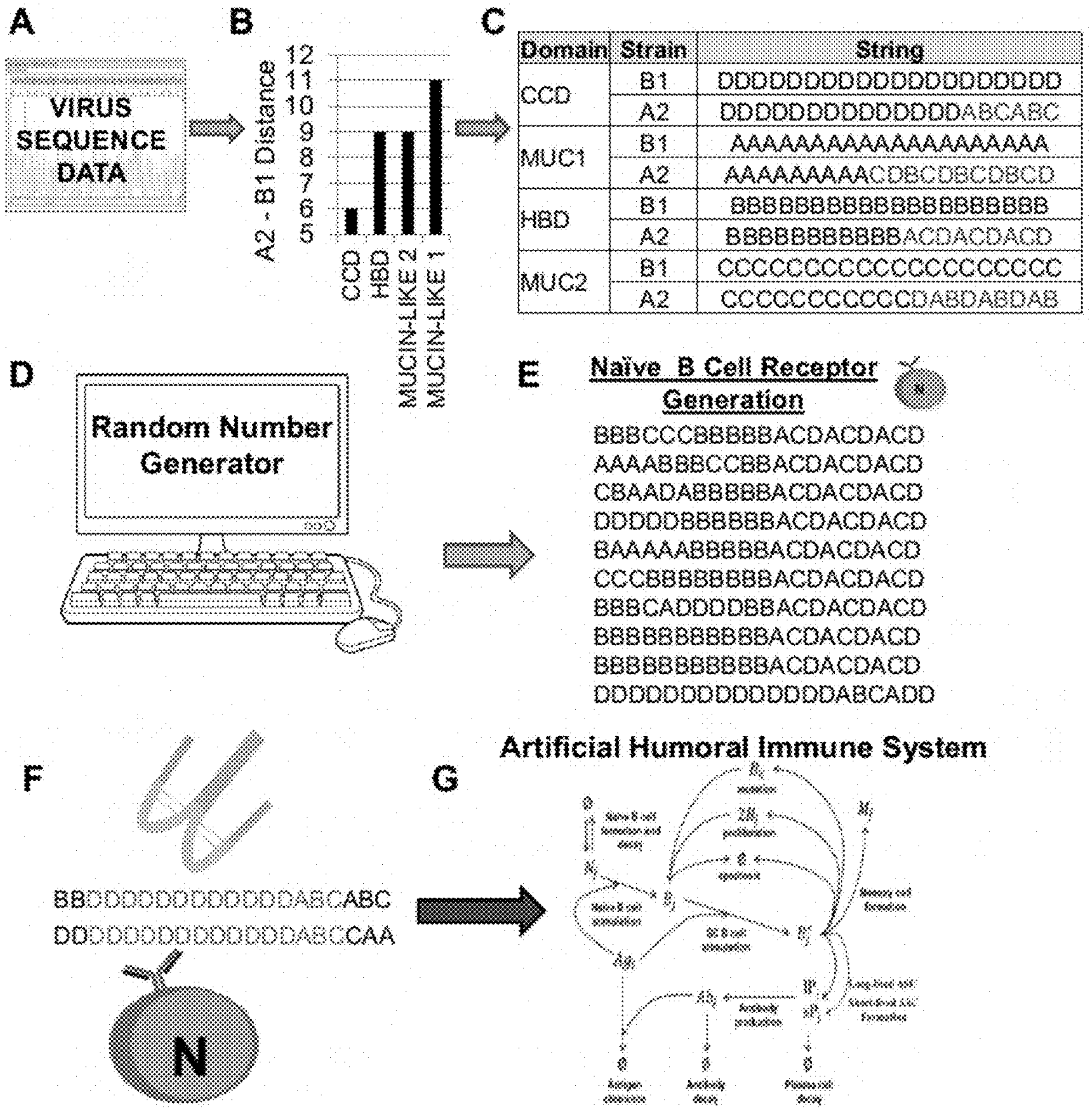
Figures 14A, 14B, 14C, 14D, 14E, 14F, and 14G

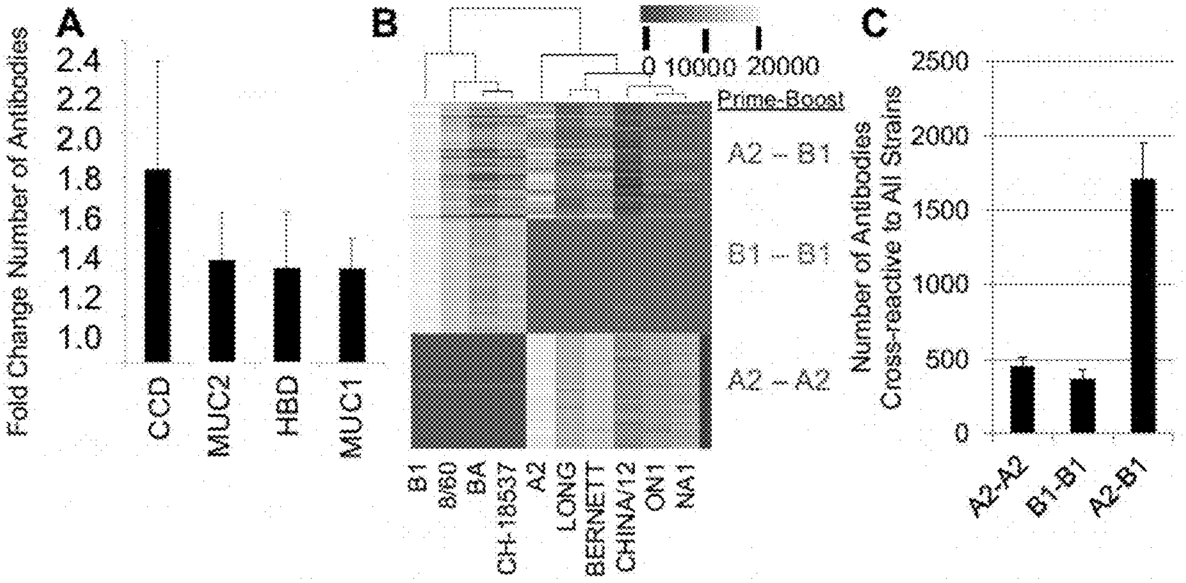
Figures 15A, 15B, and 15C
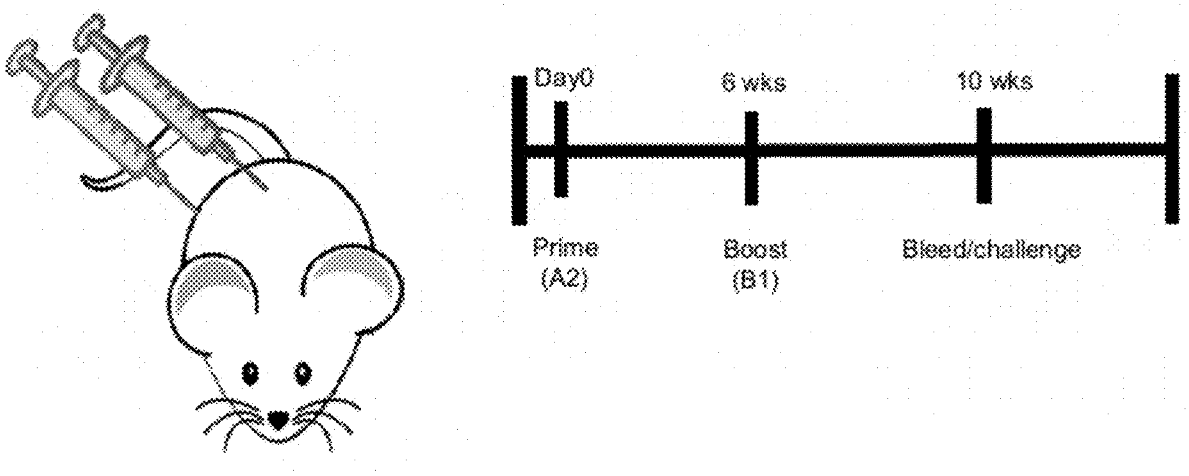
Figure 16

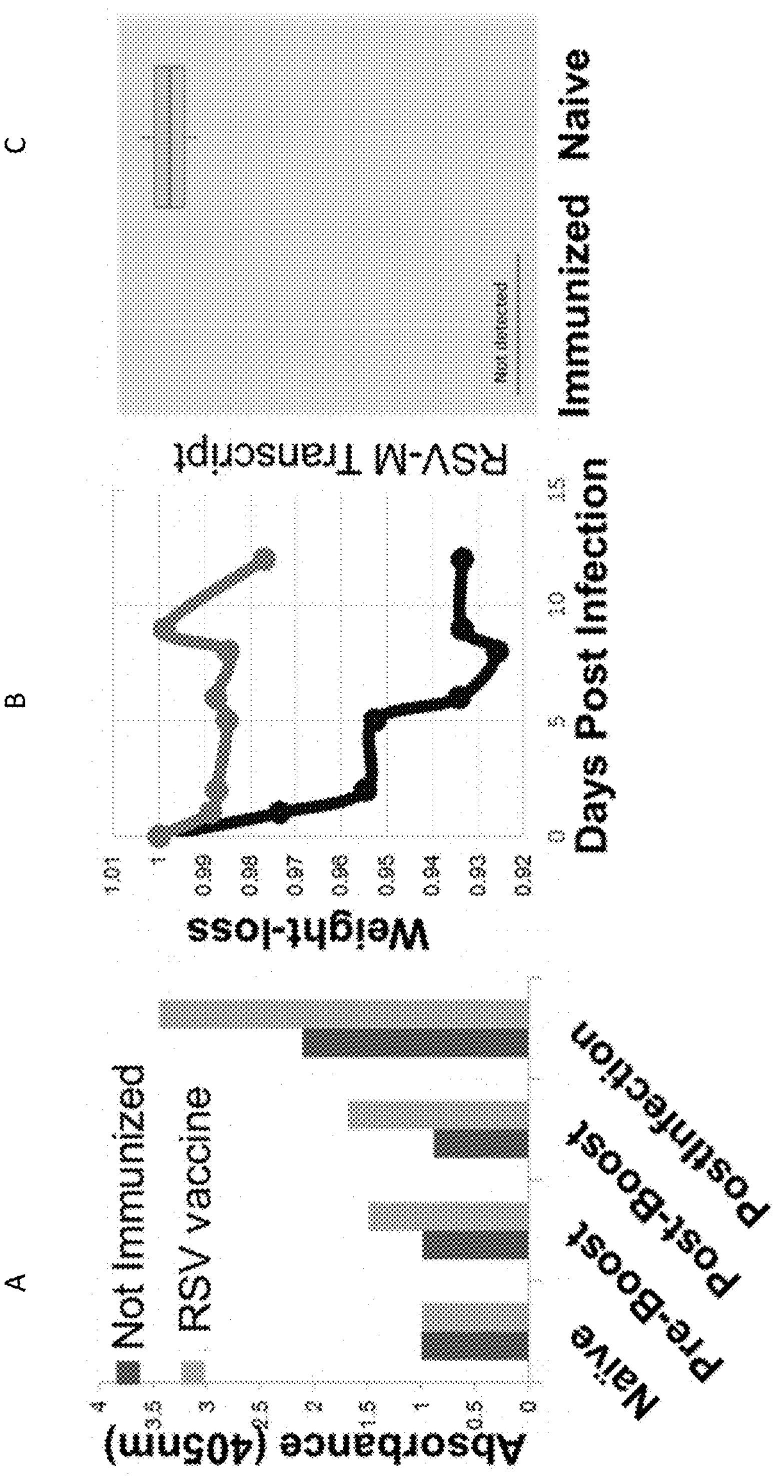
Figures 17A, 17B, and 17C

SEQUENCE LISTING

```
<160> NUMBER OF SEQ ID NOS: 23

<210> SEQ ID NO 1
<211> LENGTH: 298
<212> TYPE: PRT
<213> ORGANISM: respiratory syncytial virus

<400> SEQUENCE: 1

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295


<210> SEQ ID NO 2
<211> LENGTH: 299
<212> TYPE: PRT
```

<213> ORGANISM: respiratory syncytial virus

<400> SEQUENCE: 2

```
Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Ile Phe Ile Ile Ser
    50                  55                  60

Ala Asn His Lys Val Thr Leu Thr Thr Val Thr Val Gln Thr Ile Lys
65                  70                  75                  80

Asn His Thr Glu Lys Asn Ile Thr Thr Tyr Leu Thr Gln Val Pro Pro
                85                  90                  95

Glu Arg Val Ser Ser Ser Lys Gln Pro Thr Thr Thr Ser Pro Ile His
            100                 105                 110

Thr Asn Ser Ala Thr Thr Ser Pro Asn Thr Lys Ser Glu Thr His His
        115                 120                 125

Thr Thr Ala Gln Thr Lys Gly Arg Thr Thr Thr Ser Thr Gln Thr Asn
    130                 135                 140

Lys Pro Ser Thr Lys Pro Arg Leu Lys Asn Pro Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Lys Pro Thr Ile Lys Pro Thr Asn Lys Pro Thr Thr
        195                 200                 205

Lys Thr Thr Asn Lys Arg Asp Pro Lys Thr Pro Ala Lys Thr Thr Lys
    210                 215                 220

Lys Glu Thr Thr Thr Asn Pro Thr Lys Lys Pro Thr Leu Thr Thr Thr
225                 230                 235                 240

Glu Arg Asp Thr Ser Thr Ser Gln Ser Thr Val Leu Asp Thr Thr Thr
                245                 250                 255

Leu Glu His Thr Ile Gln Gln Gln Ser Leu His Ser Thr Thr Pro Glu
            260                 265                 270

Asn Thr Pro Asn Ser Thr Gln Thr Pro Thr Ala Ser Glu Pro Ser Thr
        275                 280                 285

Ser Asn Ser Thr Gln Asn Thr Gln Ser His Ala
    290                 295
```

<210> SEQ ID NO 3
<211> LENGTH: 42
<212> TYPE: PRT
<213> ORGANISM: respiratory syncytial virus

<400> SEQUENCE: 3

```
Ser Lys Pro Asn Asn Asp Phe His Phe Glu Val Phe Asn Phe Val Pro
1               5                   10                  15

Cys Ser Ile Cys Ser Asn Asn Pro Thr Cys Trp Ala Ile Cys Lys Arg
            20                  25                  30

Ile Pro Asn Lys Lys Pro Gly Lys Lys Thr
        35                  40
```

-continued

<210> SEQ ID NO 4
<211> LENGTH: 42
<212> TYPE: PRT
<213> ORGANISM: respiratory syncytial virus

<400> SEQUENCE: 4

```
Lys Lys Pro Lys Asp Asp Tyr His Phe Glu Val Phe Asn Phe Val Pro
1               5                   10                  15

Cys Ser Ile Cys Gly Asn Asn Gln Leu Cys Lys Ser Ile Cys Lys Thr
            20                  25                  30

Ile Pro Ser Asn Lys Pro Lys Lys Lys Pro
        35                  40
```

<210> SEQ ID NO 5
<211> LENGTH: 23
<212> TYPE: PRT
<213> ORGANISM: respiratory syncytial virus

<400> SEQUENCE: 5

```
His Phe Glu Val Phe Asn Phe Val Pro Cys Ser Ile Cys Ser Asn Asn
1               5                   10                  15

Pro Thr Cys Trp Ala Ile Cys
            20
```

<210> SEQ ID NO 6
<211> LENGTH: 23
<212> TYPE: PRT
<213> ORGANISM: respiratory syncytial virus

<400> SEQUENCE: 6

```
His Phe Glu Val Phe Asn Phe Val Pro Cys Ser Ile Cys Gly Asn Asn
1               5                   10                  15

Gln Leu Cys Lys Ser Ile Cys
            20
```

<210> SEQ ID NO 7
<211> LENGTH: 23
<212> TYPE: PRT
<213> ORGANISM: respiratory syncytial virus

<400> SEQUENCE: 7

```
His Phe Glu Val Phe Asn Phe Val Pro Cys Ser Ile Cys Ser Asn Asn
1               5                   10                  15

Pro Thr Cys Trp Ala Ile Cys
            20
```

<210> SEQ ID NO 8
<211> LENGTH: 23
<212> TYPE: PRT
<213> ORGANISM: respiratory syncytial virus

<400> SEQUENCE: 8

```
Arg Phe Glu Val Phe Asn Phe Val Pro Cys Ser Ile Cys Gly Asn Asn
1               5                   10                  15

Gln Leu Cys Lys Ser Ile Cys
            20
```

<210> SEQ ID NO 9
<211> LENGTH: 23
<212> TYPE: PRT
<213> ORGANISM: respiratory syncytial virus

<400> SEQUENCE: 9

His Phe Glu Val Tyr Asn Phe Val Pro Cys Ser Ile Cys Gly Asn Asn
1 5 10 15

Gln Leu Cys Lys Ser Ile Cys
20

<210> SEQ ID NO 10
<211> LENGTH: 23
<212> TYPE: PRT
<213> ORGANISM: respiratory syncytial virus

<400> SEQUENCE: 10

His Phe Glu Val Phe Asn Leu Val Pro Cys Ser Ile Cys Ser Asn Asn
1 5 10 15

Pro Thr Cys Trp Ala Ile Cys
20

<210> SEQ ID NO 11
<211> LENGTH: 23
<212> TYPE: PRT
<213> ORGANISM: respiratory syncytial virus

<400> SEQUENCE: 11

His Phe Glu Val Phe Asn Phe Tyr Pro Cys Ser Ile Cys Ser Asn Asn
1 5 10 15

Pro Thr Cys Trp Ala Ile Cys
20

<210> SEQ ID NO 12
<211> LENGTH: 23
<212> TYPE: PRT
<213> ORGANISM: respiratory syncytial virus

<400> SEQUENCE: 12

His Phe Glu Val Phe Asn Phe Val Pro Trp Ser Ile Cys Ser Asn Asn
1 5 10 15

Pro Thr Cys Trp Ala Ile Cys
20

<210> SEQ ID NO 13
<211> LENGTH: 23
<212> TYPE: PRT
<213> ORGANISM: respiratory syncytial virus

<400> SEQUENCE: 13

His Phe Glu Val Phe Asn Phe Val Pro Cys Gly Ile Cys Gly Asn Asn
1 5 10 15

Gln Leu Cys Lys Ser Ile Cys
20

<210> SEQ ID NO 14
<211> LENGTH: 23
<212> TYPE: PRT
<213> ORGANISM: respiratory syncytial virus

<400> SEQUENCE: 14

His Phe Glu Val Phe Asn Phe Val Pro Cys Asn Ile Cys Ser Asn Asn
1 5 10 15

Pro Thr Cys Trp Ala Ile Cys
20

<210> SEQ ID NO 15

<211> LENGTH: 23
<212> TYPE: PRT
<213> ORGANISM: respiratory syncytial virus

<400> SEQUENCE: 15

His Phe Glu Val Phe Asn Phe Val Pro Cys Ser Val Cys Gly Asn Asn
1               5                   10                  15

Gln Leu Cys Lys Ser Ile Cys
            20

<210> SEQ ID NO 16
<211> LENGTH: 23
<212> TYPE: PRT
<213> ORGANISM: respiratory syncytial virus

<400> SEQUENCE: 16

His Phe Glu Val Phe Asn Phe Val Pro Cys Ser Ile Cys Asn Asn Asn
1               5                   10                  15

Pro Thr Cys Trp Ala Ile Cys
            20

<210> SEQ ID NO 17
<211> LENGTH: 23
<212> TYPE: PRT
<213> ORGANISM: respiratory syncytial virus

<400> SEQUENCE: 17

His Phe Glu Val Phe Asn Phe Val Pro Cys Ser Ile Cys Gly Ser Asn
1               5                   10                  15

Gln Leu Cys Lys Ser Ile Cys
            20

<210> SEQ ID NO 18
<211> LENGTH: 23
<212> TYPE: PRT
<213> ORGANISM: respiratory syncytial virus

<400> SEQUENCE: 18

His Phe Glu Val Phe Asn Phe Val Pro Cys Ser Ile Cys Ser Lys Asn
1               5                   10                  15

Pro Thr Cys Trp Ala Ile Cys
            20

<210> SEQ ID NO 19
<211> LENGTH: 23
<212> TYPE: PRT
<213> ORGANISM: respiratory syncytial virus

<400> SEQUENCE: 19

His Phe Glu Val Phe Asn Phe Val Pro Cys Ser Ile Cys Gly Asn Asn
1               5                   10                  15

Arg Leu Cys Lys Ser Ile Cys
            20

<210> SEQ ID NO 20
<211> LENGTH: 23
<212> TYPE: PRT
<213> ORGANISM: respiratory syncytial virus

<400> SEQUENCE: 20

His Phe Glu Val Phe Asn Phe Val Pro Cys Ser Ile Cys Ser Asn Asn
1               5                   10                  15

-continued

```
Pro Ala Cys Trp Ala Ile Cys
            20


<210> SEQ ID NO 21
<211> LENGTH: 23
<212> TYPE: PRT
<213> ORGANISM: respiratory syncytial virus

<400> SEQUENCE: 21

His Phe Glu Val Phe Asn Phe Val Pro Cys Ser Ile Cys Gly Asn Asn
1               5                   10                  15

Gln Phe Cys Lys Ser Ile Cys
            20


<210> SEQ ID NO 22
<211> LENGTH: 23
<212> TYPE: PRT
<213> ORGANISM: respiratory syncytial virus

<400> SEQUENCE: 22

His Phe Glu Val Phe Asn Phe Val Pro Cys Ser Ile Cys Gly Asn Asn
1               5                   10                  15

Gln Leu Cys Lys Ser Phe Cys
            20


<210> SEQ ID NO 23
<211> LENGTH: 5
<212> TYPE: PRT
<213> ORGANISM: respiratory syncytial virus
<220> FEATURE:
<221> NAME/KEY: misc_feature
<222> LOCATION: (2)..(4)
<223> OTHER INFORMATION: Xaa can be any naturally occurring amino acid

<400> SEQUENCE: 23

Cys Xaa Xaa Xaa Cys
1               5
```

COMPUTATIONAL ALGORITHM FOR UNIVERSAL VACCINE SELECTION

CROSS REFERENCE TO RELATED APPLICATION

This application claims priority to U.S. Provisional Application No. 62/925,935 filed on Oct. 25, 2019 and U.S. Provisional Application No. 62/845,030 filed on May 8, 2019. The contents of the applications are incorporated herein by reference in their entireties.

FIELD OF THE INVENTION

This invention relates to methods to determine vaccine candidates that can be used to induce broadly cross-reactive immunity against pathogens, related vaccines, and related methods.

BACKGROUND OF THE INVENTION

Infectious diseases caused by pathogens, such as viruses (e.g., a Respiratory Syncytial Virus, a coronavirus, or an influenza virus), become severe in some cases depending on types of pathogens and infected subjects. For example, Respiratory Syncytial Virus (RSV) causes 65 million infections a year. RSV infects humans within two years of life and continually throughout life. There are no available licensed vaccines for RSV. Despite the dire need of the medical field for a vaccine, few academic laboratories primarily study RSV, and even fewer are researching RSV vaccines. Development of new immunization strategies would help to accelerate development of vaccine against RSV and other viruses.

Traditional vaccine strategies against pathogens such as viruses use live attenuated inactivated, or synthetic based formulations that represent a single virus strain for each subtype. Strategies that aim to induce immunity to a single viral stain do not protect against emerging, divergent viral strains and only provide protection for a few years. There are needs for novel strategies that provoke highly cross-reactive antibodies and provide protection against viral infections including RSV diseases and for a "universal" RSV vaccine.

SUMMARY OF INVENTION

This invention relates to methods to determine vaccine candidate strains for inducing broadly cross-reactive immunity against pathogens, related vaccines, and related methods.

In one aspect, the invention provides an immunogenic composition comprising an isolated or recombinant RSV G-protein or an immunogenic fragment thereof, an adjuvant, and a pharmaceutically acceptable carrier. The RSV G-protein can be from an A2 strain and comprises the sequence of SEQ ID NO: 1. The RSV G-protein can also be from a B1 strain and comprises the sequence of SEQ ID NO: 2. In some examples, the immunogenic fragment comprises a central conserved-domain (CCD), examples of which include SEQ ID Nos: 3-22 and their variants. The protein or immunogenic fragment can be 3 to 500 (e.g., 5-300, 10-200, 15-100, and 20-50) amino acids in length. Various suitable adjuvants can be used and disclosed herein. Examples include a squalene-based oil-in-water nano-emulsion. The w/v ratio of the RSV G-protein or the immunogenic fragment to the adjuvant can range from about 1/1 to about 1/20, such as about 5 micrograms to about 25 microliters per dosage unit.

In another aspect, the invention provides a method of inducing an immune response in a subject, comprising administering an effective amount of the immunogenic composition described above. Also provided is another method of inducing an immune response in a subject. The method comprises (1) administering to the subject an effective amount of a first immunogenic composition comprising a first RSV G-protein or an immunogenic fragment thereof; and (2) administering to the subject an effective amount of a second immunogenic composition comprising a second RSV G-protein or an immunogenic fragment thereof. Preferably, the second RSV G-protein or immunogenic fragment is different from the first RSV G-protein or immunogenic fragment. For example, two different polypeptides selected from SEQ ID NOs: 1-23 and their variants can be used for the two administering steps respectively.

In one embodiment, the first RSV G-protein can be from the A2 strain and comprise the sequence of SEQ ID NO: 1. In that case, the second RSV G-protein can be from B1 strain and comprise the sequence of SEQ ID NO: 2. In another embodiment, the first RSV G-protein can be from the B1 strain and comprise the sequence of SEQ ID NO: 2. In that case, the second RSV G-protein can be from the A2 strain and comprise the sequence of SEQ ID NO: 1. As mentioned above, the first immunogenic composition or the second immunogenic composition can comprise an adjuvant, such as a squalene-based oil-in-water nano-emulsion. The w/v ratio of the RSV G-protein or the immunogenic fragment to the adjuvant can range from about 1/1 to about 1/20, such as about 5 micrograms to about 25 microliters per dosage unit. In this method, the second immunogenic composition can be administered to the subject after the first immunogenic composition is administered to the subject. The time interval between administration of the first immunogenic composition and administration of the second immunogenic composition can range from about 1 to about 24 months, such as about 6 months. Examples of the immunogenic fragment include SEQ ID Nos: 3-23 and their variants.

In a further aspect, the invention provides a method of for identifying a polypeptide sequence for vaccine. The method comprises obtaining genomic sequence data of a number of strains of a pathogen (e.g., a virus); processing the sequence data via stochastic simulation; quantifying an ability of a polypeptide sequence to induce cross-reactive immunity to all strains tested, and ranking said ability. Also provided is a system for identifying candidate vaccine strains. The system comprises a non-transitory, computer readable memory, one or more processors, and a computer-readable medium containing programming instructions that, when executed by the one or more processors, cause the system to execute one or more steps of the above-described method. Examples of the virus include: RSV, coronavirus (e.g., Severe Acute Respiratory Syndrome coronavirus (SARS-CoV), Middle East Respiratory Syndrome coronavirus (MERS-CoV), or SARS-CoV-2), Ebola virus, Marburg virus, influenza viruses (e.g., influenza A virus, influenza B virus, and influenza C virus), human immunodeficiency virus (HIV), herpes simplex virus (HSV), human papilloma virus (HPV), hepatitis B virus (HBV), Epstein-Barr virus (EBV), flavivirus, Zika virus, Rhinovirus, Enterovirus, Dengue virus, yellow fever virus, Japanese encephalitis virus, and West Nile virus.

In another aspect, the invention provides an immunogenic composition comprising a polypeptide having a sequence identified by the method described above and a pharmaceutically acceptable carrier. Also provide is a method of inducing an immune response in a subject, comprising administering an effective amount of the immunogenic composition to the subject. In one example, the invention provides RSV vaccine formulations and regimens.

The details of one or more embodiments of the invention are set forth in the description below. Other features, objectives, and advantages of the invention will be apparent from the description and from the claims.

BRIEF DESCRIPTION OF THE DRAWINGS

FIGS. 11A, 11B, and 11C are diagrams showing (A) Two G-proteins are shown with a conserved target region (CCD) and highly variable other regions (Mucin-like domains 1 & 2 and the Heparin-binding domain). (B) In order to implement an immune focusing strategy hosts are first immunized with one G-protein and boost immunized with the second G-protein 6 months later. (C) During the initial immunization memory B cells specific to the first recombinant G-protein are formed, some of which are specific to the CCD region. Upon boosting with the second G-protein containing a conserved CCD region, CCD specific memory B cells are readily recalled and quickly differentiate into antibody secreting plasmablasts. Memory B cells to other regions are not recalled due to low cross-reactivity to the other variable regions.

FIGS. 12A, 12B, and 12C are diagrams showing (A) The number of amino acid differences between G-proteins of RSV strains across all strains were determined and mapped. Strains are colored by year of isolation and each point represents a single RSV strain. Historic strains and clades labeled and the bar length represents 25 amino acid differences. (B) The number of unique amino acids across all strains found at each site along the primary protein structure of the RSV G-protein. Each dot represent a single amino acid position. (C) The average amino acid differences between all RSV strains was determined for each extracellular domain of the G-protein.

FIGS. 13A, 13B, 13C, 13D, 13E, 13F, and 13G are diagrams and photographs showing: (A) CX3CR1 transcript levels and (B) CX3CR1 protein levels of PHLE cells and Hep2 cells were determined. (C) PHLE cells were infected with RSV-A2-GFP. 48 hrs post infection, flow cytometric analysis using CX3CR1 specific probes was performed. GFP expression levels in CX3CR1 positive and negative PHLE cells were compared. (D) PHLE cells were infected with RSV-A2-GFP after cells were pre-incubated for 30 minutes with (right) control antibody or (left) anti-CX3CR1 antibody (25 ug/ml). Fluorescent images were taken 24 hr post infection and (E) fluorescent foci were quantified. (F) PHLE cells pre-incubated with varying levels of anti-CX3CR1 antibody and subsequently infected with RSV-A2-GFP. RSV-M transcript levels were determined 24 hrs post infection. (G) PHLE cells were also infected with RSV-A2-GFP that was pre-incubated with recombinant CX3CR1 protein or control. RSV-M transcript levels 24 hr post infection were determined.

FIGS. 14A, 14B, 14C, 14D, 14E, 14F, and 14G are diagrams showing: (A) RSV amino acid sequence data is obtained and (B) amino acid differences for each G-protein domain are calculated, divided by domain length, and multiplied by 20 resulting in distances between 1-20 (distances between A2 and B1 RSV strains are shown). (C) Distances are used to create 20-character strings with identical differences. These strings represent antigenic sites for each domain. (D) A random number generator is used to create a (E) set of random 20-character strings representing the B cell receptor of naïve B cells in the model. (F) Antigen "units" are then added to the model where cognate naïve B cells (or memory B cells for secondary exposures) have a chance to react with the antigen. (G) Upon binding, naive B cells proliferate, differentiate, secrete antibody. Antibody removes antigen form the system.

FIGS. 15A, 15B, and 15C are diagrams showing that during the simulation antibody levels and specificities to 10 chosen antigens were tracked. (A) The average number of antibodies specific to each region of the G-protein 30 days post heterologous boost (A2-B1) relative to homologous boosting (A2-A2) was determined. (B) The average number of antibodies specific to each RSV strain used in the model at 30 days post boost with homologous (A2-A2 or B1-B1) or heterolgous (A2-B1) antigen. Each row represents a single simulation with the condition noted on the y-axis. (C) The average number of highly cross-reactive antibodies, those cross-reactive to all 10 RSV strains used in the model, for each prime-boost condition was determined.

FIG. 16 shows an example of a method for confirming simulation findings using murine model.

FIGS. 17A, 17B, and 17C are a set of diagrams showing vaccine formulations disclosed herein were effective in a murine challenge model to provide protection against RSV infection. Mice were immunized with computer optimized vaccine formulations by a two-part immunization regimen. 30 days post immunization the mice were challenged with an RSV A2-19F strain. (A) Blood was drawn and serum obtained prior to immunization, pre-boost (6 weeks post priming), post-boost (28 days after boosting), and 10 days after challenge with the A2-19F RSV strain. Total IgG serum antibody specific to RSV G-protein was measured by indirect-ELISA. (B) Weight was measured for each mouse after RSV challenge for 12 days in mice immunized with the vaccine formulation and unimmunized mice. Three mice were used per group. (C) RSV virus load as measured by RSV-M gene transcript levels in lung after RSV challenge.

DETAILED DESCRIPTION OF THE INVENTION

Figure 1:
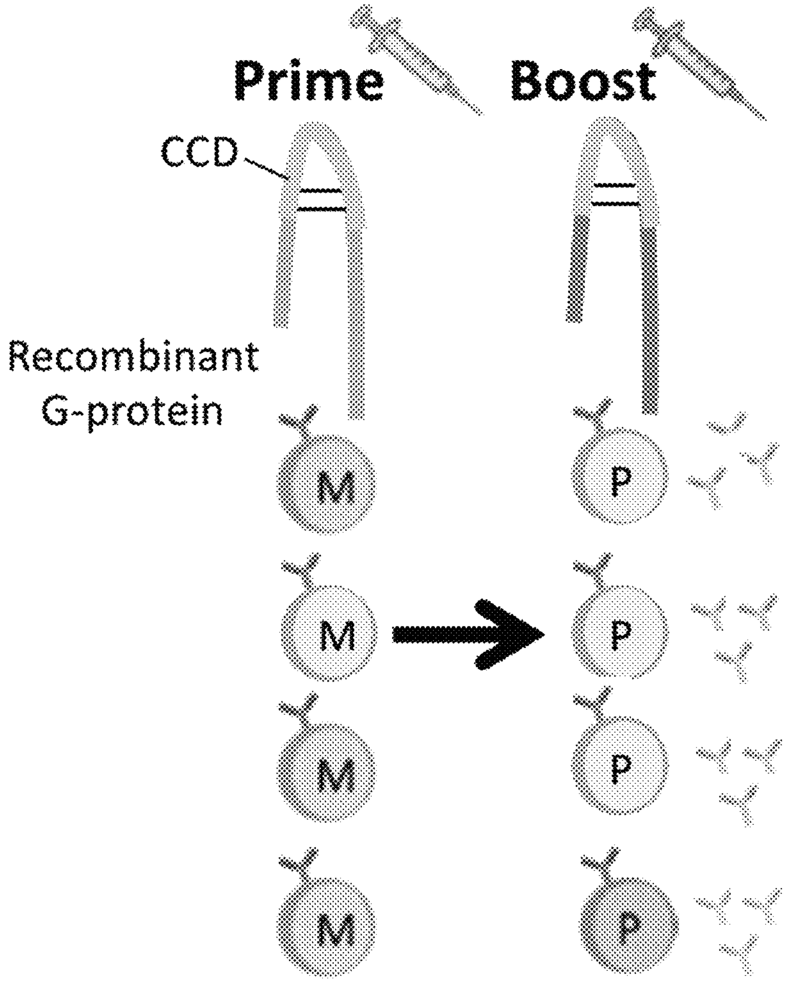
FIG. 1 shows an immune focusing schematic. Memory cells are formed after immunization with recombinant G-protein, some of which are specific to the CCD region. Upon boosting with an antigenically distinct G protein containing a conserved CCD region, CCD specific memory B cells are preferentially activated and differentiated into antibody secreting plasmablasts.

This invention relates to methods to determine vaccine candidates that can be used to induce broadly cross-reactive immunity against pathogens, related vaccines, and related methods.

Methods for Identifying Vaccine Candidates

Conventional methods exist for identifying candidate antigens for vaccine development. Yet, conventional vaccine development approaches have thus far been limited and are largely dependent upon hit-and-trial methodologies. The conventional methods are not applicable to non-cultivable organisms like viruses. Furthermore, modern regulatory authorities now require vaccines to meet higher standards of safety and physico-chemical characterization The present invention provides methodologies, systems and computer-implemented methods for identifying vaccine candidates. The method and its algorithm disclosed herein can be used to select one or more vaccine candidates for any pathogen with sufficient genetic sequence data. A feature of many such methods is a procedure for identifying amino acid residues in a protein sequence that are predicted to affect a desired activity, such as broadly cross-reactive immunogenic activity. As one example, such a method and algorithm include (1) sequence quality control and processing, (2) functional motif identification, (3) amino acid variation calculator, (4) simulation pre-processing, (5) simulation of immune responses to candidate strains, (6) optimization and ranking of vaccine candidate strains, and (7) output, vaccine strain selection rank.

In one embodiment, the method and algorithm include the following steps: (1) publicly available pathogen genomic sequence data is obtained, (2) a computational algorithm processes the sequence data and performs stochastic simulations, (3) the resulting data is then used to quantify a vaccine candidate's ability to induce cross-reactive immunity to all strains tested, and (4) a list of ranked vaccine candidate strains (and associated regimens) are output. This method has a number of advantages. It is fully computational and easily executed. It can use previously collected virus genome data and provide a rank of a vaccine candidate strains. Using that, one can screen hundreds of thousands of virus strains rapidly. It is easy to use, fast, and repeatable.

Another aspect of the present invention provides a computer-readable medium storing a computer program executable by a computer for performing any of the methods disclosed in this application. A computer program product is provided for use in conjunction with a computer having one or more memory units and one or more processor units. The computer program product comprises a computer readable storage medium having a computer program mechanism encoded thereon, where the computer program mechanism can be loaded into the one or more memory units of the computer and cause the one or more processor units of the computer to execute steps comprising performing any of the methods disclosed in this application. In some embodiments, the computer program mechanism can be loaded into the one or more memory units of the computer, and cause the one or more processor units of the computer to optionally execute steps comprising outputting to a user, a user interface device, a monitor, a computer-readable storage medium, a computer-readable memory, or a local or remote computer system; or displaying, a result of the method, for example, as is applicable to the method being executed, a sequence of the identified amino acid residues, one or more parameters of a pathogen or an antigen, or an indication (e.g., a probability) of immunization outcome or disease condition.

In some examples shown below, the method is used to identify vaccine candidates to induce broadly cross-reactive immunity against human RSV.

RSV and RSV Polypeptides

RSV infection is so universal that almost everyone is infected within the first 2 years of life. Each year, 2-5% of these infections can result in severe disease. Moreover, over 50,000 childhood deaths occur each year. RSV continues to infect individuals throughout their lifetime with increasing cases of severity occurring in the elderly. All together RSV causes significant morbidity and mortality and yet no vaccine (and very limited therapeutics) exist that protect against RSV disease. Recent advances in the methodology of influenza vaccinology bring forth new perspectives into RSV immunization strategies to induce protective immunity towards RSV.

RSV is categorized into two subtypes, A and B, based on large genetic and antigenic differences between strains. Antigenic and genetic diversity also occurs within subtypes and a spectrum of antigenically distinct RSV strains now circulate in the population. A successful immunization strategy should induce antibodies cross-reactive against current and future circulating strains and provide protection from RSV disease. Induction of antibodies that disrupt virus binding to the lung epithelial cell membrane is one method of conferring protection against viral disease.

RSV circulates in the human population as a diverse number of uniquely genetic strains. RSV encodes 10 genes that express 11 proteins, including three surface proteins (G, F, and SH) and 8 internal proteins. The surface attachment glycoprotein (G-protein) contains a CCD region, which is almost completely conserved across subtypes. The CCD is indicated in binding CX3CR1 on the surface lung epithelial cells. Monoclonal antibodies specific to the CCD region can neutralize both subtypes and are protective in mice. Based on the conservation of this region and its functional importance, increasing the CCD specific antibodies can result in immunity that is highly cross-reactive and protects from RSV disease.

Evolutionary rates of the virus are similar to other RNA viruses with estimates of $1.83\text{-}1.95\times10^{-3}$ nucleotide substitutions/site/year. These high mutation rates of RSV produce an evolutionary landscape that allows quick adaption of RSV to host immunity pressures. Much of the genetic changes occur in the host attachment proteins on the surface the virus. The greatest genomic variation occurs in the G-protein, although genetic difference can be found among all viral proteins. Unlike other regions of the G-protein, the inner-loop of the G-protein, the CCD, is highly conserved. Induction of antibodies to the CCD region have been shown to be cross reactive to both A and B RSV subtypes induction of antibodies cross-reactive to this functional, highly-conserved domain of RSV have been shown to reduce RSV disease. Taken together, CCD is a prime target for an RSV vaccine.

Studies have allowed one to appreciate the role that memory B cells play during repeat vaccination. Moreover, these studies have demonstrated that by extorting the lower activation threshold and higher replication rates of memory B cells, one can direct the immune response to particular regions of the virus. If this region is highly conserved, then boosting antibodies to this region may boost the cross-reactivity of the immune response. This disclosure calls this phenomenon "immune focusing" (FIG. 1) and an immune focusing strategy is possible with RSV. The expectation is that this may produce immunity to regions of the viruses that do not undergo antigenic drift.

Figure 2:
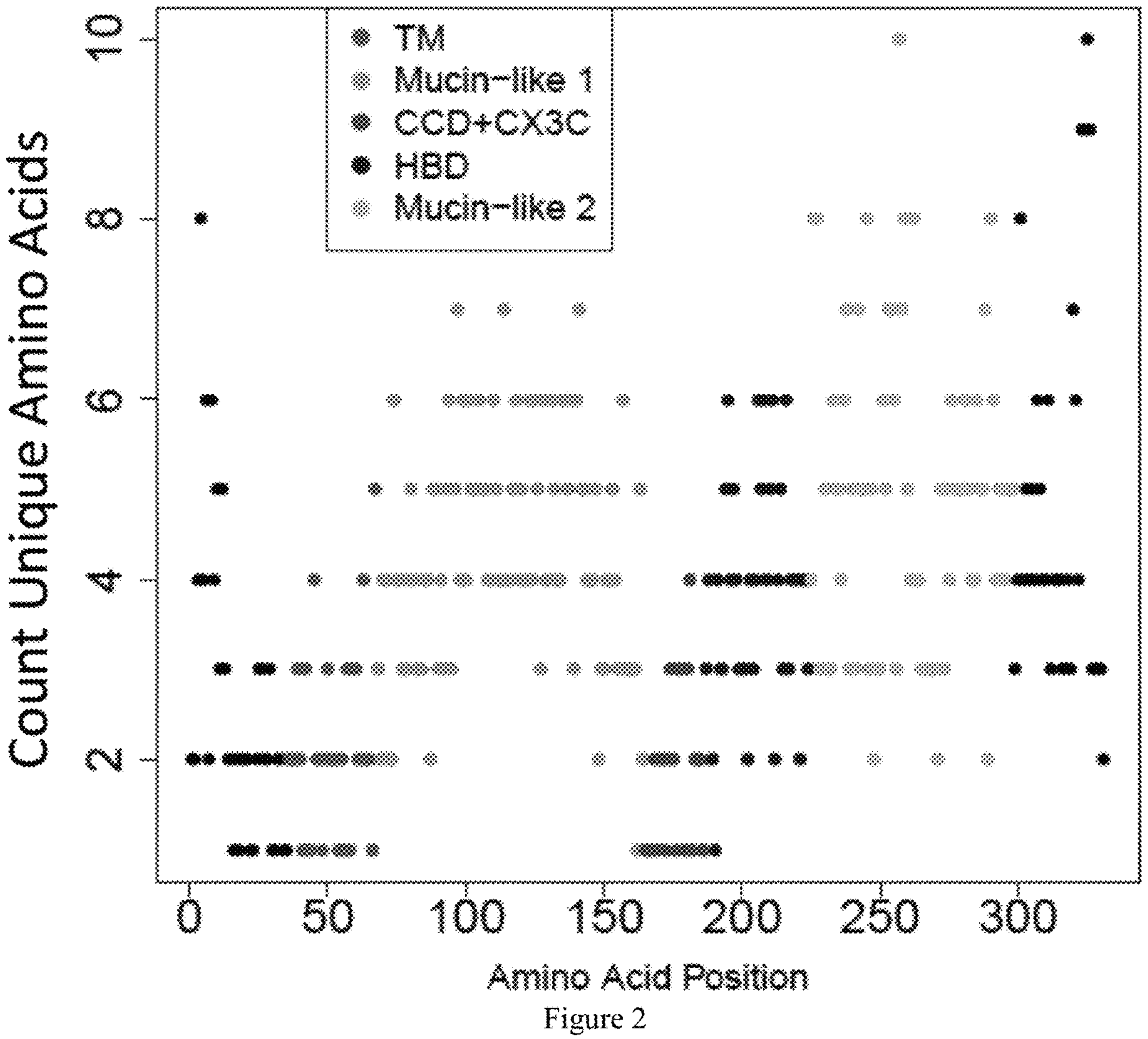
FIG. 2 shows amino acid variations across G-proteins. Number of types of amino acids at each position of the linear G-protein. Analysis performed on publicly available sequences data from >1000 strains (both subtypes).

Although the G-protein is highly variable, the G-protein contains a highly conserved region (FIG. 2). This property makes the G-protein amenable to an immune focusing strategy. The CCD forms part of an inter-protein loop and contains a CXXXC (SEQ ID No: 23) or CX3C motif that is 100% conserved within subtypes and highly conserved between subtypes. Therefore, antibodies that target this domain often bind strains from both subtypes.

Listed below are sequences of two exemplary RSV G-Proteins:

AF035006 (A2):

(SEQ ID NO: 1)

Msknkdqrtaktlertwdtlnhllfissclyklnlksvaqitlsilamii
stsliiaaiifiasanhkvtpttaiiqdatsqikntt ptyltqnpqlgis
psnpseitsgittilasttpgvkstlqsttvktknttttqtqpskpttkq
rqnkppskpnndfhfevfnfvpcsicsnnptCWAICkripnkkpgkkttt
kptkkptlkttkkdpkpqttkskevpttkpteeptinttktniittllts
nttgnpeltsqmetfhstssegnpspsqvsttseypsqpssppntprq

AF013254 (B1):

(SEQ ID NO: 2)

mskhknqrtartlektwdtlnhlivissclyrlnlksiaqialsvlamii
stsliiaaiifiisanhkvtlttvtvqtiknhteknittyltqvppervs
sskqptttspihtnsattspntksethhttaqtkgrtttstqtnkpstkp
rlknppkkpkddyhfevfnfvpcsicgnnqlCKSICktipsnkpkkkpti
kptnkpttkttnkrdpktpakttkketttnptkkptlttterdtstsgst
vldtttlehtiqqqslhsttpentpnstqtptasepstsnstqntqsha.

In the above sequences, the CX3C motifs (aa. 182-186) are shown in upper cases. A central conserved domain (CCD) is bold and underlined (aa. 164-186, SEQ ID Nos: 5 and 6, respectively). A longer, central conserved region (aa. 157-198) is bold in each of the two sequences (SEQ ID Nos: 3 and 4, respectively). A number of CCD variants are listed in Table 1 below.

In addition to conservation, the CCD is a highly functional region of the virus. The CCD region has been shown to bind the fractalkine receptor (CX3CR1) on human lung epithelial cells facilitating the attachment of the virus to the host and alter cellular transcription and cytokine levels of host cells. The secreted form of the G-protein has also been shown to modulate immune cells during RSV infection. Monoclonal antibodies that bind to this region have been shown to potently neutralize both RSV subtypes (A and B). Given both the conservation and the functional significance of the CCD domain, enhancing antibody responses to this region can provide the neutralizing efficacy and cross-reactivity needed for an effective universal RSV vaccine.

TABLE 1

| 164 | 165-167 | 168 | 169 | 170 | 171 | 172 | 173 | 174 | 175 | 176 | 177 | 178 | 179 | 180 | 181 | 182 | 183 | 184 | 185 | 186 | SEQ ID NO: |
|---|---|---|---|---|---|---|---|---|---|---|---|---|---|---|---|---|---|---|---|---|---|
| h | fev | f | n | f | v | p | c | s | i | c | s | n | n | p | t | c | w | a | i | c | 7 |
| r | fev | f | n | f | v | p | c | s | i | c | g | n | n | q | I | c | k | s | i | c | 8 |
| h | fev | y | n | f | v | p | c | s | i | c | g | n | n | q | I | c | k | s | i | c | 9 |
| h | fev | f | n | I | v | p | c | s | i | c | s | n | n | p | t | c | w | a | i | c | 10 |
| h | fev | f | n | f | y | p | c | s | i | c | s | n | n | p | t | c | w | a | i | c | 11 |
| h | fev | f | n | f | v | p | w | s | i | c | s | n | n | p | t | c | w | a | i | c | 12 |
| h | fev | f | n | f | v | p | c | g | i | c | g | n | n | q | I | c | k | s | i | c | 13 |
| h | fev | f | n | f | v | p | c | n | i | c | s | n | n | p | t | c | w | a | i | c | 14 |
| h | fev | f | n | f | v | p | c | s | v | c | g | n | n | q | I | c | k | s | i | c | 15 |
| h | fev | f | n | f | v | p | c | s | i | c | n | n | n | p | t | c | w | a | i | c | 16 |
| h | fev | f | n | f | v | p | c | s | i | c | g | s | n | q | I | c | k | s | i | c | 17 |
| h | fev | f | n | f | v | p | c | s | i | c | s | k | n | p | t | c | w | a | i | c | 18 |
| h | fev | f | n | f | v | p | c | s | i | c | g | n | n | r | I | c | k | s | i | c | 19 |
| h | fev | f | n | f | v | p | c | s | i | c | s | n | n | p | a | c | w | a | i | c | 20 |
| h | fev | f | n | f | v | p | c | s | i | c | g | n | n | q | f | c | k | s | i | c | 21 |
| h | fev | f | n | f | v | p | c | s | i | c | g | n | n | q | I | c | k | s | f | c | 22 |

As disclosed herein, CCD specific antibodies are highly cross-reactive and reduce RSV disease. More specifically, levels of CCD specific human serum antibody is correlated with CX3CR1 specific virus neutralization. Additionally, a computer-optimization approach is used to develop an immunization strategy in mice in order to induce CCD specific antibody and test if induction of CCD specific antibody leads to increased antibody cross-reactivity. Last, it is demonstrated that an immunization strategy that increases CCD specific antibody leads to increased protection against RSV disease in mice.

The inventor's group have performed estimation of the antigenic variation between over a thousand RSV strains and developed a computation model that can simulate the humoral immune response to the RSV G-protein. Using these results, the inventor's group have identified a set of vaccine candidate strains predicted to boost CCD specific antibody. The inventor's group have also developed assays to measure CCD specific serum antibody in humans and mice. Additionally, the inventor's group have developed a mouse model of immunization with recombinant G-proteins capable of inducing G-protein specific antibody responses.

This disclosure investigates the role of CCD specific human serum antibodies on virus neutralization. This disclosure also provides optimized immune focusing strategies using computer simulations and tests these strategies to boost cross-reactive serum antibody in mice. Lastly, this disclosure describes if vaccination strategies that induce CCD specific antibody reduce disease in mice challenged with RSV. The studies described below both test and evaluate CCD as a target for a universal vaccine strategy.

This disclosure provides measurements of CCD specific antibodies in a large human cohort. It also demonstrates that a CCD specific human antibody is potently neutralizing RSV and reduces infection severity in mice. Furthermore, this disclosure provides the first evidence that a prime-boost strategy can be used to focus the antibody response to the CCD of RSV G-protein.

In one embodiment, human serum is used to demonstrate if CCD specific antibody is induced naturally by infection. Using a newly developed ELISA-based approach to CCD specific antibody measurement, the CCD antibody levels are measured across a panel of human sera. These studies provide the first estimates of CCD specific antibodies in the human population. Additionally, the studies measure the ability of each serum to neutralize viruses from both subtypes in vitro and demonstrate the association of CCD specific antibodies and neutralization capacity. These studies provide the first evidence that CCD specific antibody in human serum is potently neutralizing.

In another embodiment, a CCD inducing immunization strategy is optimized using computer simulations. The model allows prediction of the relative antibody levels to different regions across the G-protein expected after immunization with recombinant G-protein. This work provides the first comprehensive antigenic estimates of RSV strains that have circulated since the 1950s. Studies of this disclosure also test a large number of immunization strategies and provide predictions of antigenic-site-specific antibody levels to a large range of RSV antigens. These predictions provide innovation in immunization strategies predicted to induce the greatest increase in CCD specific antibodies. Applying these strategies in mice provides insight into how immunization strategies can be used to induce CCD specific antibodies.

In a further embodiment, a murine model is used to test whether increasing CCD specific antibody can reduce disease. This disclosure provides estimates of disease reduction upon challenging mice with RSV after receiving different immunization strategies. Weight loss and virus load can be measured after challenge. This embodiment provides insights into an immune focusing strategy for RSV.

Taken together the studies described here help target specific regions of RSV. They provide CCD specific antibody level estimates in the human population. They also demonstrate immunization strategies capable of inducing CCD specific antibody and if CCD specific antibody levels affect disease burden after challenge with RSV. Furthermore, the studies aim to provide a path towards development of a universal RSV vaccine.

In addition, this disclosure also provides the following:

A novel ELISA-based assay for detection of CCD specific antibody.

A high-throughput physiological assay to measure RSV neutralization capacity of serum.

A method to estimate antigenic variation across RSV strains;

First-of-a-kind computation model to simulate immune responses to RSV immunogens;

A method of using alternative computer models to reduce the number of animals used in experimentation.

Demonstrating for the first-time seroconversion after heterologous prime-boost immunization of mice with recombinant RSV G-protein.

Demonstrating infection of mice with a fluorescent reporter RSV.

Creating recombinant G-proteins to six RSV strains and related plasmids.

The tremendous impact on public health cause by RSV can no longer be ignored and the research community has been called on to provide a solution. This application seeks to bring the knowledge of influenza universal vaccine strategies to the field of RSV and allows the development of novel assays and computational tools to advance RSV vaccine design. Using these tools, this disclosure provides a pathway for development of a universal RSV vaccine for pre-clinical trials and the necessary models needed to accurately test the ability of the vaccine to protect against RSV infection.

This disclosure incorporates in vitro, in silico, and in vivo models to practice the invention. It first establishes the levels CCD specific human serum antibody that exists naturally in the population. It also tests if higher levels of CCD specific serum antibody correlate with greater virus neutralization. Additionally, computer simulations are used to optimize an immune focusing strategy that aims to increase CCD specific antibody in mice and increase antibody cross-reactivity. Finally, using challenge studies, different vaccine strategies are evaluated on their abilities to reduce RSV infection in mice. The findings here provide evidence of CCD as a universal vaccine target, advance computational models to understand RSV disease, and test immune-focusing vaccination strategies to protect against RSV disease.

Immunogenic Compositions and Uses Thereof

The RSV polypeptides of the invention may be formulated as a vaccine (also referred to as an "immunogenic composition") according to methods well known in the art. Such compositions will typically include immune stimulants to enhance immune responses. The optimal ratios of each component in the formulation may be determined by techniques well known to those skilled in the art. The immunogenic compositions may be administered to a patient or subject according to standard techniques well-known to those of skill in the art. The subject will typically be a human or non-human animal (e.g., cattle, horses, pigs, dogs, and cats). The human patient or subject may be an adult and child. In a typical case, the subject will be an infant (e.g., a newborn), a young child, a pregnant mother, a woman of childbearing age, or the elderly.

The immunogenic compositions may also comprise one or more of the RSV polypeptides shown in SEQ ID NOs: 1-23 or a multimeric RSV polypeptide comprising one of more the polypeptide sequences. The polypeptide may be unglycosylated or glycosylated.

Preparation and use of immunogenic compositions are well known to those of skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

Polynucleotides encoding the RSV polypeptides of the invention can also be administered to the subject. Typically, an expression cassette suitable for driving expression in human cells is prepared. This approach is described, for instance, in Wolff (1990) Science 247:1465-1468; U.S. Pat. Nos. 5,580,859 and 5,589,466.

The RSV polypeptides may also be expressed in replication deficient or competent viral vectors that comprise nucleic acids encoding them. Such viral vectors include, for example, adenoviral vectors, vaccinia virus vectors, avipox vector such as fowlpox or canarypox, herpes virus vectors, a vesicular stomatitis virus vectors, or alphavirus vectors. One of skill will recognize that the immunogenic compositions of the invention may comprise multiple antigens and vectors. In such embodiments, the viral vector can act as an immune stimulant. Thus, the immune stimulant of the immunogenic compositions of the invention will be the vector itself and addition of further immune stimulants may not be necessary.

The RSV polypeptides may also be administered in combination with nanoparticles (i.e., particulate material with size 1-1000 nm). A great variety of materials can be used to prepare nanoparticles useful in the immunogenic compositions of the invention. For example, synthetic polymers such as poly(d,l-lactide-co-glycolide) (PLG), poly(d, l-lactic-coglycolic acid)(PLGA), poly(g-glutamic acid) (g-PGA), polyethylene glycol) (PEG) and polystyrene can be conveniently used. Polymeric nanoparticles entrap the RSV polypeptides for delivery to certain cells or sustain antigen release as a result of their slow biodegradation rate. Natural polymers based on polysaccharide may also be used. Examples include pullulan, alginate, inulin and chitosan. Inorganic nanoparticles useful in the invention include gold nanoparticles, which can be surface-modified with carbohydrates, carbon nanoparticles or silica-based nanoparticles.

The compositions are suitable for single administrations or a series of administrations. When given as a series, inoculations subsequent to the initial administration are given to boost the immune response and are typically referred to as booster inoculations. The compositions of the invention can be used as a boosting composition primed by antigen using any of a variety of different priming compositions, or as the priming composition. Thus, one aspect of the present invention provides a method of inducing and/or boosting an immune response to an antigen in an individual.

The timing of the administration of boosting compositions is well within the skill in the art. Boosting composition are generally administered weeks or months after administration of the priming composition, for example, about 2-3 weeks or 4 weeks, or 8 weeks, or 16 weeks, or 20 weeks, or 24 weeks, or 28 weeks, or 32 weeks, or 1 month, or 2 months, or 3 months, or 4 months, or 5 months, or 6 months, or 7 months, or 8 months, or 9 months, or 10 months, or 11 months, or 12 months, or 18 months, or 24 months.

The compositions of the invention may comprise other RSV immunogens or the priming or boosting inoculations may comprise other immunogens. The other immunogens used in combination with the RSV polypeptides of the invention are not critical to the invention. Examples of such immunogens can also include those from Influenza, Hepatitis and other childhood infectious diseases.

The immunogens in the respective priming and boosting compositions (however many boosting compositions are employed) need not be identical, but can share epitopes. The immunogen may correspond to a complete antigen in a target pathogen or cell, or a fragment thereof. Peptide epitopes or artificial strings of epitopes may be employed, more efficiently cutting out unnecessary protein sequence in the antigen and encoding sequence in the vector or vectors. For example, one or more additional epitopes may be included, for instance epitopes, which are recognized by T helper cells, especially epitopes, recognized in individuals of different HLA types.

As noted above, the immunogenic compositions of the invention may comprise an immune stimulant (also referred to as an adjuvant). In those embodiments in which the RSV polypeptide is expressed in a viral vector, the immune stimulant can typically the viral vector, itself. Adjuvants suitable for co-administration in accordance with the present invention should be ones that are potentially safe, well tolerated and effective in people including QS-21, Detox-PC, MPI,-SE, MoGM-CSF, TiterMax-G, CRL-1005, GERBU, TERamide, PSC97B, Adjumer, PG-026, GSK-I, CieMAF, B-alethine, MPC-026, Adjuvax, CpG ODN, Betafectin, Alum, and MF59.

Other immune stimulants that may be administered include lectins, growth factors, cytokines and lymphokines such as alpha-interferon, gamma interferon, platelet derived growth factor (PDGF), granulocyte-colony stimulating factor (GCSF), granulocyte macrophage colony stimulating factor (GMCSF), tumor necrosis factor (TNF), epidermal growth factor (EGF), IL-1, IL-2, IL-4, IL-6, IL-8, IL-10, and IL-12 or encoding nucleic acids therefore.

As noted above, the compositions of the invention may comprise a pharmaceutically acceptable excipient, carrier, buffer, stabilizer or other materials including particles (e.g., nanoparticles) well known to those skilled in the art. Such materials should be non-toxic and should not interfere with the efficacy of the active ingredient. The precise nature of the carrier or other material may depend on the route of administration, e.g., oral, intravenous, cutaneous or subcutaneous, intramucosal (e.g., gut), intranasal, intramuscular, or intraperitoneal routes. Administration is typically intradermal, e.g., subcutaneous or intramuscular.

Intramuscular administration of the immunogenic compositions may be achieved by using a needle to inject a suspension of the RSV polypeptide or nucleic acid encoding it. An alternative is the use of a needless injection device to administer the composition (using, e.g., BIOJECTOR) or a freeze-dried powder containing the vaccine.

For intravenous, cutaneous or subcutaneous injection, or injection at the site of affliction, the RSV polypeptide will be in the form of a parenterally acceptable aqueous solution that is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection, Preservatives, stabilizers, buffers, antioxidants and/or other additives may be included, as required. A slow-release formulation may also be employed.

Typically, administration will have a prophylactic aim to generate an immune response against a RSV antigen before infection or development of symptoms. Diseases and disorders that may be treated or prevented in accordance with the present invention include those in which an immune response may play a protective or therapeutic role. In other embodiments, the RSV polypeptides can be administered for post-exposure prophylactics.

The immunogenic compositions containing the RSV polypeptide or polynucleotides encoding them are administered to a subject, giving rise to an anti-RSV immune response in the subject. An amount of a composition sufficient to in induce a detectable immune response is defined to be an "immunologically effective dose." As shown below, the immunogenic compositions of the invention induce an antibody response, as well as a CD8+ cell immune response. In a typical embodiment, the immune response is a protective immune response.

The actual amount administered, rate, time-course of administration, will depend on the nature, and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

In one exemplary regimen, the RSV polypeptide is administered (e.g., intramuscularly) at a dose of 1 micrograms to 1 milligram/injection. A boost can be administered later. The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

The compositions of the invention may be administered alone or in combination with other treatments, either simultaneously or sequentially dependent upon the condition to be treated. Accordingly, the present invention further provides a method for generating, enhancing, or modulating a protective and/or therapeutic immune response to RSV in a subject. The method includes administering to a subject in need of therapeutic and/or preventative immunity one or more of the compositions described herein. In this method, the composition includes an isolated polypeptide or a fragment, variant, or derivative thereof, for example, a recombinant protein, a purified subunit, or viral vector expressing the protein, as described above.

Definitions

The terms "adjuvant" and "immune stimulant" are used interchangeably herein, and are defined as one or more substances that cause stimulation of the immune system. The stimulation will augment or modify the immune response, e.g., by intensifying or broadening the specificity of either or both the antibody and the cellular immune response to the RSV polypeptide. In this context, an adjuvant or immune stimulant is used in the immunogenic compositions of the invention to enhance an immune response to RSV proteins. In the case where the RSV polypeptide is expressed in a viral vector, the viral vector can act as the immune stimulant.

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation).

A "recombinant" peptide, polypeptide, or protein refers to a peptide, polypeptide, or protein produced by recombinant DNA techniques; i.e., produced from cells transformed by an exogenous DNA construct encoding the desired peptide. A "synthetic" peptide, polypeptide, or protein refers to a peptide, polypeptide, or protein prepared by chemical synthesis. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Within the scope of this invention are fusion proteins containing one or more of the afore-mentioned sequences and a heterologous sequence. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

An "isolated" peptide, polypeptide, or protein refers to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein described in the invention can be purified from a natural source, produced by recombinant DNA techniques, or by chemical methods.

A "variant" of a polypeptide comprises an amino acid sequence wherein one or more amino acid residues are inserted into, deleted from and/or substituted (e.g., conservative modification) into the amino acid sequence relative to another polypeptide sequence. Variants include fusion proteins. A "derivative" of a polypeptide is a polypeptide that has been chemically modified in some manner distinct from insertion, deletion, or substitution variants, e.g., via conjugation to another chemical moiety.

A conservative modification or functional equivalent of a peptide, polypeptide, or protein disclosed in this invention refers to a polypeptide derivative of the peptide, polypeptide, or protein, e.g., a protein having one or more point mutations, insertions, deletions, truncations, a fusion protein, or a combination thereof. It retains substantially the activity to of the parent peptide, polypeptide, or protein (such as those disclosed in this invention). In general, a conservative modification or functional equivalent is at least 60% (e.g., any number between 60% and 100%, inclusive, e.g., 60%, 70%, 75%, 80%, 85%, 90%, 95%, 96%, 97%, 98%, and 99%) identical to a parent (e.g., one of SEQ ID NOs: 1-23). Accordingly, within scope of this invention are peptide, polypeptide, or protein having one or more point mutations, insertions, deletions, truncations, a fusion protein, or a combination thereof.

As used herein, the term "conservative modifications" refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include: amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

As used herein, the percent homology between two amino acid sequences is equivalent to the percent identity between the two sequences. The percent identity between the two sequences is a function of the number of identical positions shared by the sequences (i.e., % homology=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the) XBLAST program (version 2.0) of Altschul, et al. (1990) J. Mol. Biol. 215:403-10. BLAST protein searches can be performed with the) (BLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays.

The term "isolated nucleic acid molecule" refers to a single or double-stranded polymer of deoxyribonucleotide or ribonucleotide bases read from the 5' to the 3' end or an analog thereof, that has been separated from at least about 50 percent of polypeptides, peptides, lipids, carbohydrates, polynucleotides or other materials with which the nucleic acid is naturally found when total nucleic acid is isolated from the source cells. Preferably, an isolated nucleic acid molecule is substantially free from any other contaminating nucleic acid molecules or other molecules that are found in the natural environment of the nucleic acid that would interfere with its use in polypeptide production or its therapeutic, diagnostic, prophylactic or research use.

The term "vector" means any molecule or entity (e.g., nucleic acid, plasmid, bacteriophage or virus) used to transfer protein coding information into a host cell. In some embodiments, a "vector" refers to a delivery vehicle that (a) promotes the expression of a polypeptide-encoding nucleic acid sequence; (b) promotes the production of the polypeptide therefrom; (c) promotes the transfection/transformation of target cells therewith; (d) promotes the replication of the nucleic acid sequence; (e) promotes stability of the nucleic acid; (f) promotes detection of the nucleic acid and/or transformed/transfected cells; and/or (g) otherwise imparts advantageous biological and/or physiochemical function to the polypeptide-encoding nucleic acid. A vector can be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors.

The term "expression vector" refers to a linear or circular DNA molecule that comprises a segment encoding a polypeptide of interest (e.g., an RSV protein of the invention) operably linked to additional segments that provide for its transcription. Such additional segments include promoter and terminator sequences, and may also include one or more origins of replication, one or more selectable markers, an enhancer, a polyadenylation signal, and the like. Expression vectors are generally derived from bacterial or viral DNA, and may contain elements of both.

As used herein, "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antigenic agent," "antigen," or "immunogen" means a substance that induces a specific immune response in a host animal. It can be a molecule containing one or more epitopes (either linear, conformational or both) that elicit an immunological response. The term "epitope" refers to basic element or smallest unit of recognition by an individual antibody, B-cell receptor, or T-cell receptor, and thus the particular domain, region or molecular structure to which said antibody or T-cell receptor binds. An antigen may consist of numerous epitopes while a hapten, typically, may possess few epitopes.

The term "immunogenic" refers to a capability of producing an immune response in a host animal against an antigen or antigens. This immune response forms the basis of the protective immunity elicited by a vaccine against a specific infectious organism.

"Immune response" refers to a response elicited in an animal, which may refer to cellular immunity (CMI), humoral immunity or both. As used herein, the term "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4+ or CD8+ T cell, or the inhibition of a Treg cell.

The terms "priming" or "primary" and "boost" or "boosting" as used herein may refer to the initial and subsequent immunizations, respectively, i.e., in accordance with the definitions these terms normally have in immunology. However, in certain embodiments, e.g., where the priming component and boosting component are in a single formulation, initial and subsequent immunizations may not be necessary as both the "prime" and the "boost" compositions are administered simultaneously.

The term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier or excipient" refers to a carrier medium or an excipient which does not interfere with the effectiveness of the biological activity of the active ingredient(s) of the composition and which is not excessively toxic to the host at the concentrations at which it is administered. The term includes, but is not limited to, a solvent, a stabilizer, a solubilizer, a tonicity enhancing agent, a structure-forming agent, a suspending agent, a dispersing agent, a chelating agent, an emulsifying agent, an anti-foaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof. The use of such agents for the formulation of pharmaceutically active substances is well known in the art (see, for example, "Remington's Pharmaceutical Sciences", E. W. Martin, 18th Ed., 1990, Mack Publishing Co.: Easton, Pa., which is incorporated herein by reference in its entirety).

A pharmaceutically acceptable carrier or excipient, after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model. The term "animal" includes all vertebrate animals including humans. In particular, the term "vertebrate animal" includes, but not limited to, humans, canines (e.g., dogs), felines (e.g., cats); equines (e.g., horses), bovines (e.g., cattle), porcine (e.g., pigs), as well as in avians. In a preferred embodiment, the subject is a human. The terms "subject" and "patient" are used interchangeably herein to refer to a vertebrate, preferably a mammal, more preferably a human.

As used herein, the term "therapeutically effective amount" of a compound of the present invention refers to an amount of the compound of the present invention that will elicit the biological or medical response of a subject, or ameliorate symptoms, slow or delay disease progression, or prevent a disease, etc. In one embodiment, the term refers to the amount that inhibits or reduces viral colonization or infection. When applied to an individual active ingredient, administered alone, the term refers to that ingredient alone. When applied to a combination, the term refers to combined amounts of the active ingredients that result in the therapeutic effect, whether administered in combination, serially or simultaneously.

A "prophylactically effective amount" is an amount of a pharmaceutical composition that, when administered to a subject, will have the intended prophylactic effect, e.g., preventing or delaying the onset (or reoccurrence) of the disease state, or reducing the likelihood of the onset (or reoccurrence) of the disease state or associated symptoms. The full therapeutic or prophylactic effect does not necessarily occur by administration of one dose, and may occur only after administration of a series of doses. Thus, a therapeutically or prophylactically effective amount may be administered in one or more administrations.

The terms "prevent," "preventing" and "prevention" generally refer to a decrease in the occurrence of disease or disorder in a subject. The prevention may be complete, e.g., the total absence of the disease or disorder in the subject. The prevention may also be partial, such that the occurrence of the disease or disorder in the subject is less than that which would have occurred without embodiments of the present invention. "Preventing" a disease generally refers to inhibiting the full development of a disease.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" refers to within 10%, preferably within 5%, and more preferably within 1% of a given value or range. Alternatively, the term "about" refers to within an acceptable standard error of the mean, when considered by one of ordinary skill in the art. Other meanings of "about" may be apparent from the context, such as rounding off, so, for example "about 1" may also mean from 0.5 to 1.4.

EXAMPLES

Example 1. Increased CCD Specific Human Antibody Levels Are Associated with Increased Virus Neutralization Inventor' studies have suggested that variable levels of CCD specific antibody exist in the population. This variation provides an opportunity to test the effect of greater levels of CCD specific antibody on RSV neutralization. Higher levels of CCD specific serum antibody are associated with increased neutralization efficacy. Levels of naturally occurring CCD specific antibodies are first measured in a large human cohort. Using a high-throughput in vitro virus infection model, the neutralization capacity of each serum is determined. Using rigorous statistical modeling, assays are carried out to test if there is a statistically association between CCD specific antibody in serum and virus neutralization efficacy.

1.1 Measurement of CCD Specific Antibodies in Human Serum.

Figures 3A, 3B:
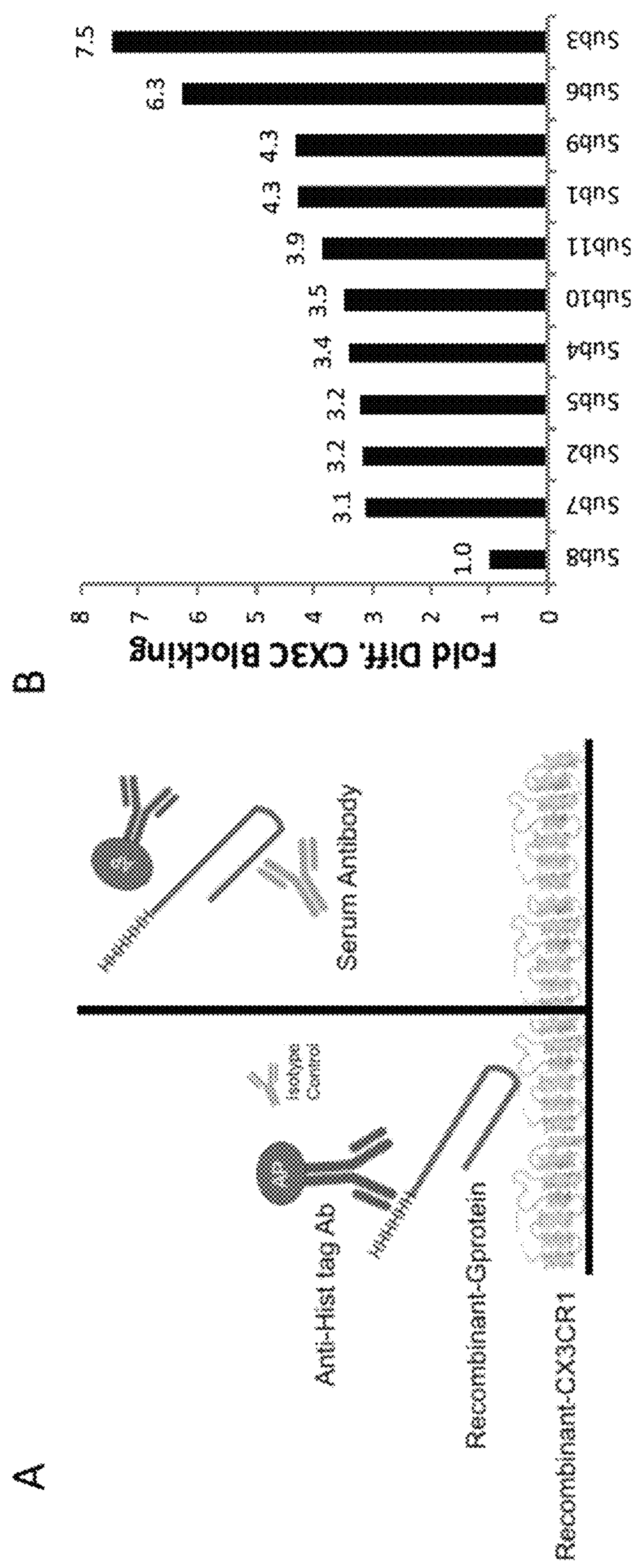
FIGS. 3A and 3B show measurement of CCD specific serum antibody. (A) Schematic of ELISA-based CCD specific antibody quantification assay. (B) Relative amounts of CCD specific antibodies normalized by total G-protein antibody levels. Sera from 11 subjects ages 1.6-46 years.

An enzyme-linked immunosorbent assay (ELISA)-based method was developed for indirect quantification CCD specific antibody (FIG. 3A). By exploiting that the CCD region binds CX3CR1, the amount of G-protein binding to CX3CR1 can be measured with or without pre-incubation with serum. In this way, the relative decrease in G-protein binding can be measured as a surrogate for the CCD specific avidity of the serum antibody. Recombinant G-protein from subtype A (A2 strain) and B (B1 strain) have been obtained from BEI Resources. CCD specific serum antibody levels from approximately 300 subjects are measured. Using this novel assay, studies demonstrate that CCD specific serum antibody varies between subjects (FIG. 3B). Given that total G-protein antibody can be affected by the timing of most recent RSV infection, serum volumes can be normalized by total G-protein antibody levels as measured by indirect-ELISA. Detection for both CCD-specific and total G-protein antibody binding can be measured using colorimetric assay (alkaline-phosphate conjugated secondary antibody) and absorbance can be obtained for each serum sample. Inventor's group have obtained pooled human plasma (RESPIGAM) which contains a high concentration of RSV specific antibodies. In order to numerate the absorption values, a standard curve using pooled human serum can be created and a four-parameter logistic curve can be fitted. Absorption values for each serum sample can be compared to the standard curve in order to allow accurate quantification. Using this approach, the proportion of CCD specific antibody levels in human serum can be determined.

1.2 Quantification of the Virus Neutralization Efficacy of Human Serum.

Figures 4A, 4B:
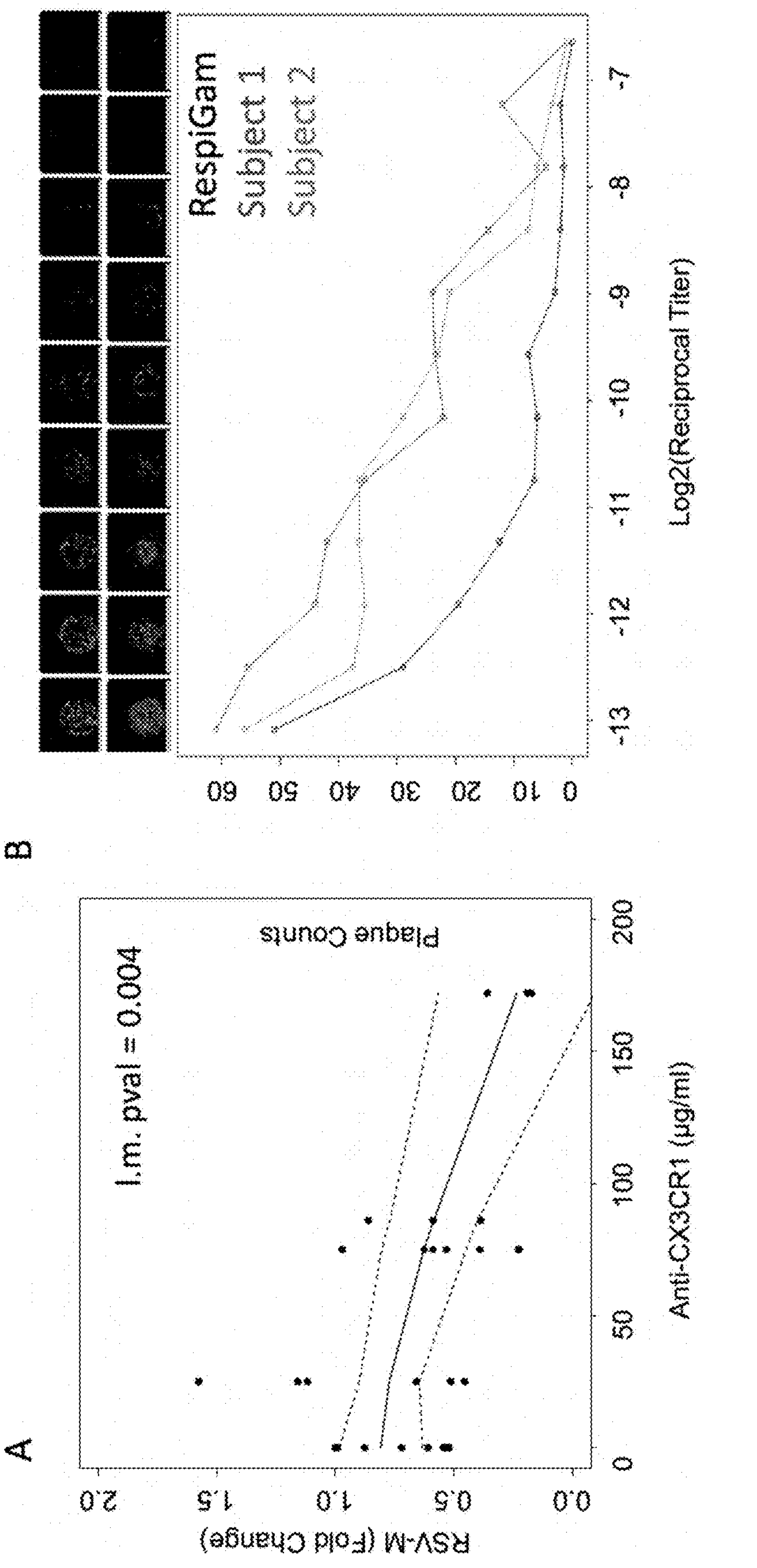
FIGS. 4A and 4B show virus neutralization assay. (A) RSV-M gene transcript levels of 16HBE cells post infection with RSV (A2 strain) pre-incubated with variable levels of anti-CX3CR1 blocking antibody. (B) 16HBE cells plated onto 96 well transwell plates and put at air-liquid interface for 7 days. Cells were infected with RSV after pre-incubation with different dilutions of human serum. Plaques were determined using CELIGO Imaging cytometer. Representative images from CELIGO (top). Plaque counts for serial dilutions of sera for two subjects and RepiGam (bottom). N=3.

Inventor's group have developed a high-throughput method of performing virus neutralization assays in vitro. The method uses the human bronchial epithelial cell line, 16HBE. 16HBE cells express CX3CR1 and demonstrate an increase in markers of differentiation, and barrier function, after placed at air-liquid interface (FIG. 4A). Cells are grown on 96-well transwell plates (CORNING HTS Transwell) to allow high-throughput assaying. Serum volumes are normalized by total G-protein antibody and serially diluted. The serum dilution needed to reduce the virus load by 50% (E.D. 50) can be determined. The RSV A2 strain contains a fluorescent reporter and virus load is quantified using a CELIGO Imaging cytometer (FIG. 4B). In order to account for variation across batches and control for quality, a standard curve using RESPIGAM pooled serum can be run on each plate. Inventor's group have obtained an RSV mutant strain containing a mutation in the CCD region that abolishes binding of the virus to CX3CR1. To determine specificity, neutralization assays can also be performed using the mutant virus.

1.3 Statistical Comparison of CCD Specific Antibodies and Virus Neutralization.

Using the data gathered in the manner described above, inventor's group statistically test the relationship between CCD specific antibody and virus neutralization. A mixed-effects linear model (Eq 1) was used to model the relationship between neutralization capacity of serum and CCD antibody levels while controlling for other variables.

$$Ni \sim Ei+Bi \quad \text{(Eq 1)}$$

Where Ni represents the E.D. 50 quantifications for each serum, Ei represents the CCD specific antibody quantification. In order to correct for any batch specific differences, a batch variable, Bi is included. Using this model one can formally test whether an increase in CCD specific antibody correlates with an increase in neutralization efficacy of the serum. In addition to the linear mixed-effects model, Pearson and Spearman correlations are also performed. Linear relationships and correlations can also be performed using E.D. 50 values obtained from the mutant RSV strain. Inventor expects high correlation between wild-type virus neutralization and CCD specific antibody with modest, or no correlation between CCD specific antibody and mutant virus neutralization.

Accurately measuring CCD specific serum antibody is of significant importance. The accuracy of the ELISA-based approach to CCD specific antibody quantification can be determined by comparing results with those from a traditional competition ELISA approach which uses an antibody-binding fragment (Fab) specific to the CCD region (obtained from Dr. Walsh). One can also use a CCD peptide-based ELISA and related antibody-binding assay. This assay can serve as a secondary method to confirm the accuracy of the CCD specific antibody measurement disclosed herein.

Some serum components, such as fractalkine, may interfere with the ELISA. Purified IgG antibody using G-protein-G beads (provided by Dr. Topham) offers an easy purification method. Resulting IgG antibody can be quantified used standard protein quantification assays (e.g., Bradford Assay). CCD specific antibody level measurements can be compared with and without IgG purification.

Although the 16HBE model demonstrates many aspects of a primary cell system, cell lines sometimes may not reflect what occurs naturally. As an alternative approach, one can use primary human epithelial cells at air-liquid interface from both children and adults. Although this system is variable from subject to subject, this may provide a more physiological system for testing neutralization and provide a method to confirm the 16HBE findings.

Example 2. Increasing CCD Specific Antibody Leads to Broader Cross-Reactivity

Given the conservation of the CCD across RSV strains, increases in CCD specific antibody can lead to increases in antibody cross-reactivity. Increasing CCD specific antibody in mice can increase cross-reactivity. Using a computer model of the humoral immune system similar to a previously reported influenza model (Anderson et al. BMC Bioinformatics 2018, 2018 Feb. 12; 19(1):51. doi: 10.1186/s12859-018-2042-4 and Anderson et al. Scientific Reports 2018, Sci Rep. 2017 Nov. 6; 7(1):14614. doi: 10.1038/s41598-017-14931-7), a prime-boost RSV immunization strategy was developed to increase CCD specific antibody levels in mice. Serum from mice immunized with the optimized strategy can be tested for reactivity against G-proteins from a wide-range of RSV strains. Statistical tests can be carried out to find out if an immunization strategy that increases CCD specific antibody levels in mice result in greater cross-reactive serum antibody levels compared to serum from mice prime-boost immunized with homologous antigen.

2.1. Development of a Computer-Optimized Immunization Strategy to Increase CCD Specific Antibody.

Figures 5A, 5B:
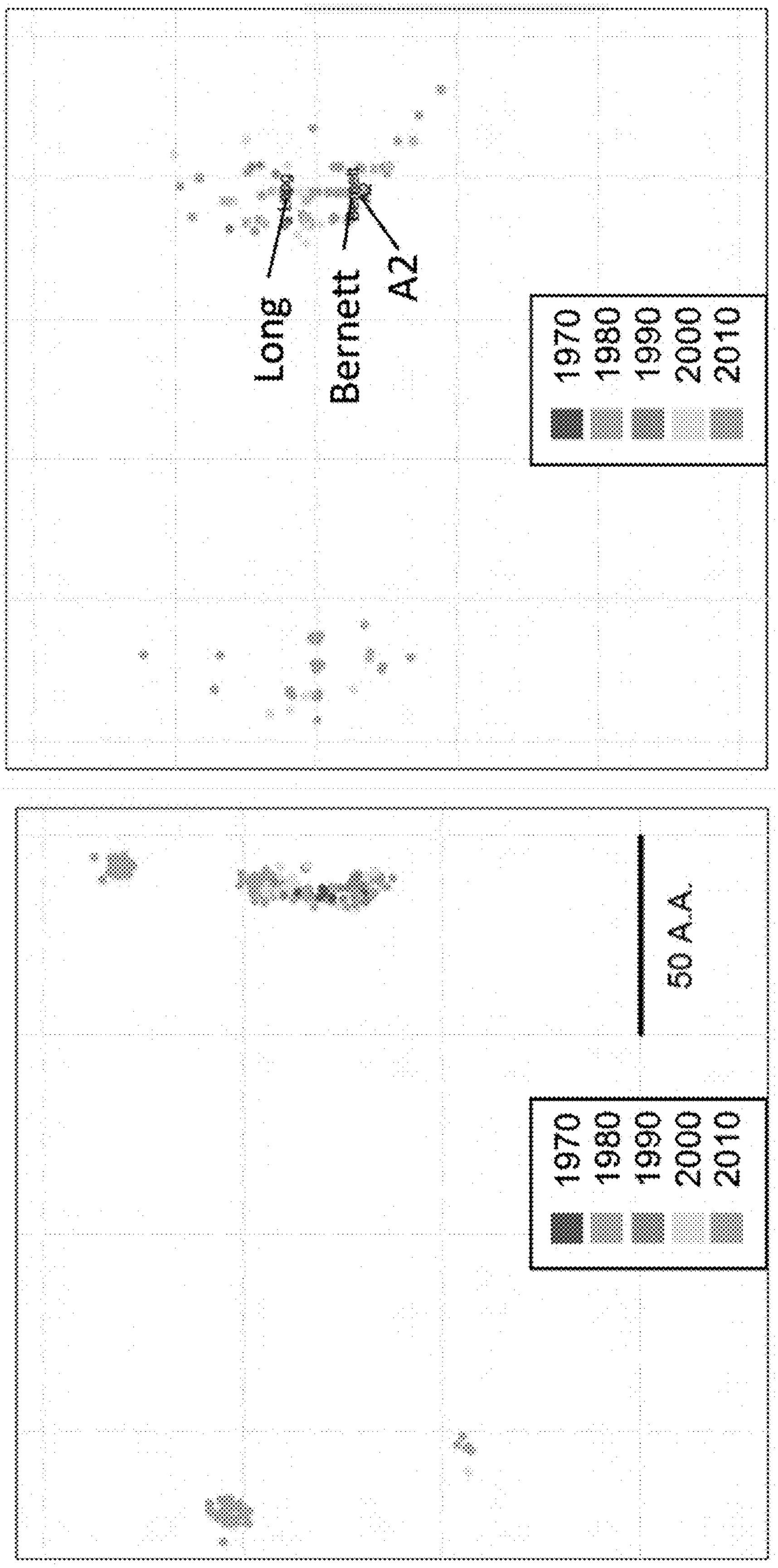
FIGS. 5A and 5B show antigenic cartography of RSV G-proteins. (A) Sequence based antigenic distance calculations were performed on G-protein sequence data from 1622 RSV strains. Principal coordinate analysis was performed on the resulting antigen distance matrix. Virus strains are represented as points on the graph and the distances between them reflects their antigenic distance. Scale bar represents 50 amino acid differences. (B) Heparin-binding domain-specific antigenic distance estimates.

In order to simulate immune responses to G-protein antigen, the antigenic distances between G-proteins from RSV strains are estimated with a method to calculate antigenic distances using viral sequence data (Anderson et al. BMC Bioinformatics 2018, 2018 Feb. 12; 19(1):51. doi: 10.1186/s12859-018-2042-4, Anderson et al. Scientific Reports 2018, Sci Rep. 2017 Nov. 6; 7(1):14614. doi: 10.1038/s41598-017-14931-7, and Anderson et al. PLoS One 2016. Aug. 5; 11(8):e0160510. doi: 10.1371/journal.pone.0160510). Using a similar method, the inventor's group have estimated the antigenic distance between thousands of G-protein RNA sequences from both local and publicly available sources (FIG. 5).

Figures 6A, 6B:
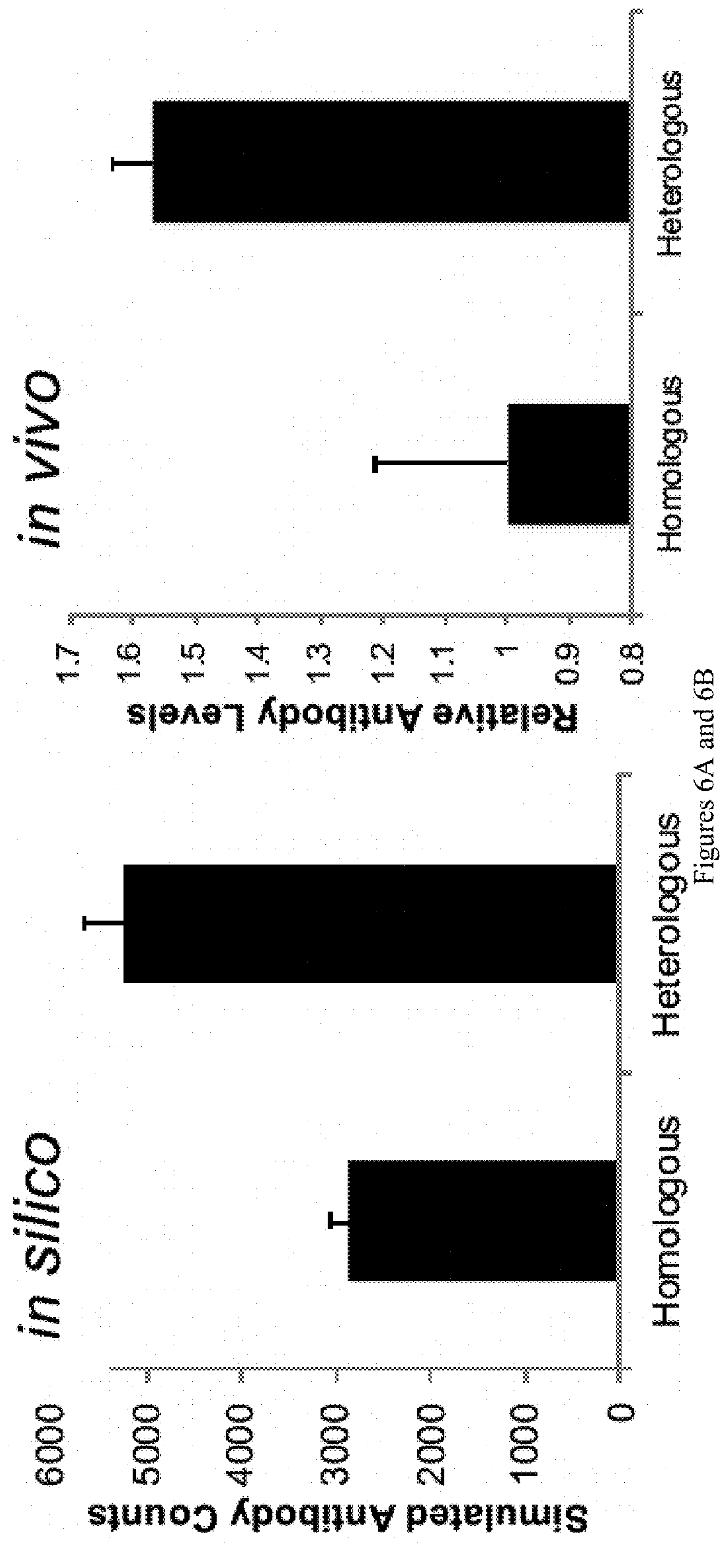
FIGS. 6A and 6B show computer-optimized influenza immunization. (A) Computer simulated HA stalk-specific antibody levels after heterologous or homologous prime-boost immunization. (B) Relative mouse serum HA stalk-specific antibody levels after homologous or heterologous prime boosting.
Figures 7A, 7B:
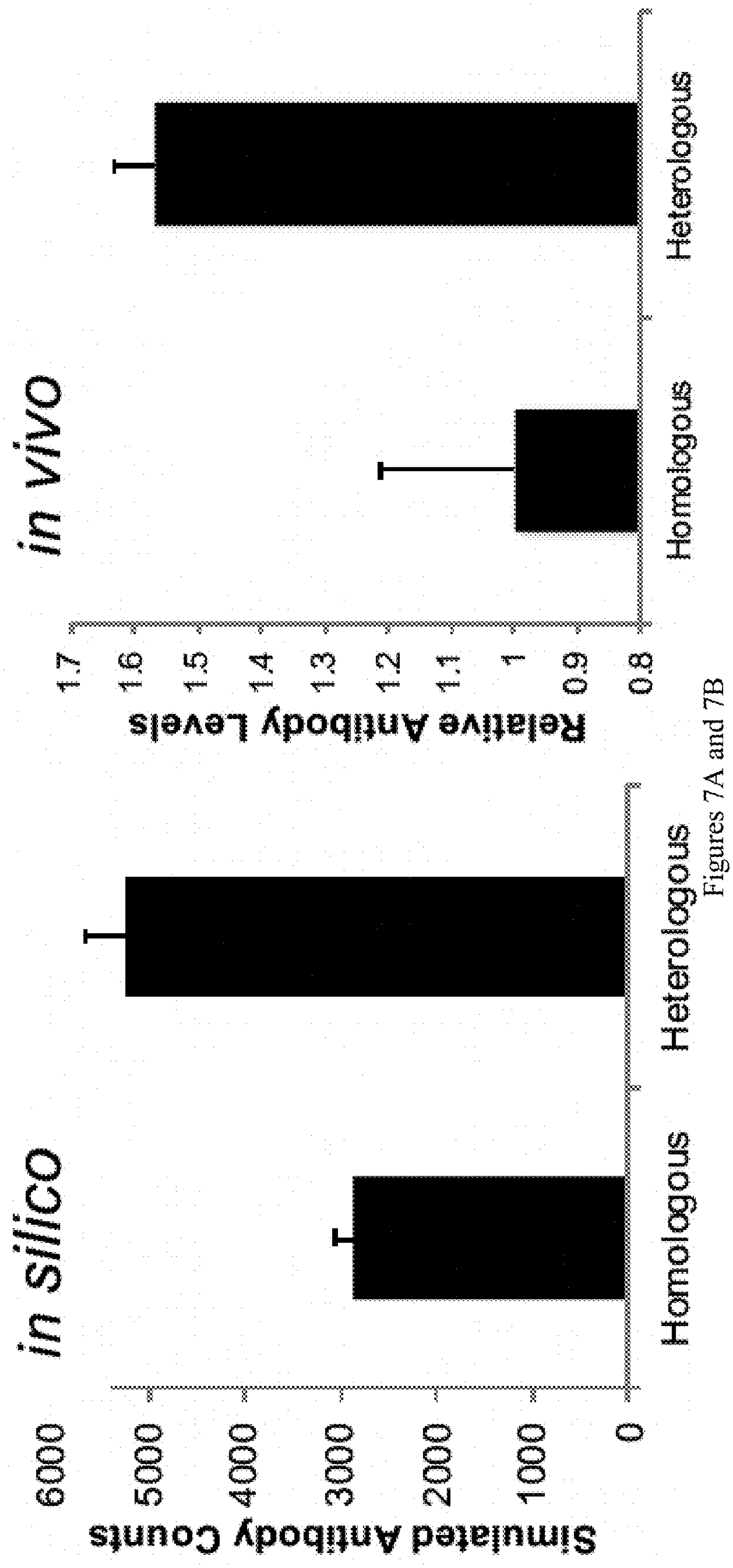
FIGS. 7A and 7B show simulating immune focusing strategies. (A) Schematic of Agent Based Computational Model. The model uses antigenic distances between G-proteins as input and uses a stochastic simulation approach to model the humoral immune response. The model tracts antibody abundance and specificity. (B) Simulated antibody levels after homologous or heterologous prime boosting with B1 and A2. Values represent the fold difference in the total number of antibodies between heterologous and homologous prime boost immunization specific to each domain. N=20.

The inventor's group also performed computer simulations to determine immunizations strategy that boosts antibody levels to the conserved "stalk" region of the influenza virus hemagglutinin and successfully tested this strategy in mice (FIG. 6). Using a similar model (FIG. 7A), the inventor's group simulate immune responses to large random sampling (>1000) of combinations of prime-boost RSV G-protein antigen pairs. Results can be compared to homologous prime and boosting to identify strategies that lead to the greatest increases in CCD specific antibody. Studies using the model have found that heterologous prime boosting with B1 and A2 strains significantly increased CCD specific antibody levels compared to homologous prime-boost (FIG. 7B). Using this model, the inventor's group simulate other pairs of G-protein antigens in order to identify prime-boost pairs that induced the greatest level of CCD specific antibody. These pairs can be chosen for immunizations in mice.

2.2. Boosting CCD Specific Antibody in Mice.

Using the predicted optimal strains in subsection 2.1, recombinant G-proteins expressing plasmids can be commercially synthesized and recombinant protein can be produced using HEK293-S cells and purified using high-pressure liquid chromatography. Recombinant G-protein structural integrity can be determined by assessing binding to CX3CR1 by ELISA and binding of L9 monoclonal antibody (obtained from Dr. Walsh) by indirect-ELISA. BALB/c mice (Jackson Lab) can be primed boost immunized with recombinant G-protein as done in the computer model. Mice can be immunized by injection with 5 micrograms of recombinant G-protein into posterior thigh muscle. Sera can be taken 28 days post boost immunization. CCD specific and total G-protein serum antibody levels can be evaluated by ELISA. CCD specific serum antibody levels can be compared to homologous prime-boost immunization.

2.3. Measuring Cross-Reactivity of Mouse Serum.

Figure 8:
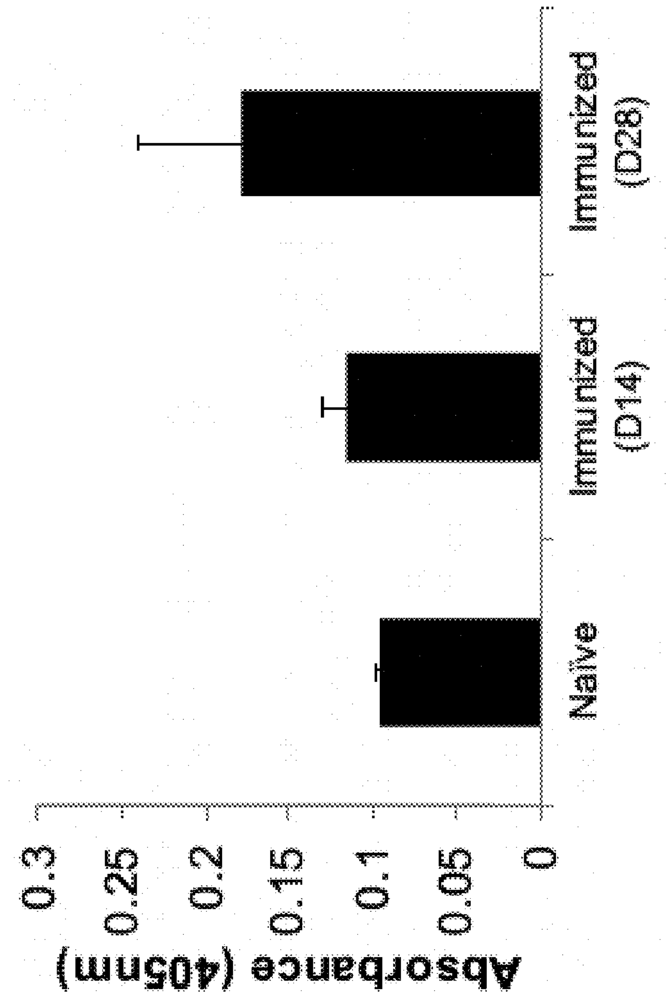
FIG. 8 shows immunization of mice with recombinant G-protein. Total A2 G-protein antibody levels after immunization of 8-wk-old Balb/C mice with recombinant A2 G-protein. Serum was taken day 0, 14, and 28 post immunization. Levels were measured by ELISA. N=4.

Tests are carried out to examine if an immunization strategy that increases CCD specific antibody levels increases cross-reactivity of serum antibody. Binding of serum antibody from mice immunized in subsection 2.2 can be determined against G-proteins from two older strains (A2 strain, subtype A; B1 strain, subtype B), two moderately recent strains (B/*Homo sapiens*/USA/87I-072A01/1987 and A/*Homo sapiens*/USA/86E-018-01/1986) and two very recent strains (and A/Shiraz/12/2016 and B/Shiraz/21/2016). Serum binding can be measured by indirect ELISA (FIG. 8). To formally test that the approach disclosed herein increases antibody cross-reactivity, statistical comparison between homologous prime-boost and the optimized immunization strategy can be compared using multivariate multiple regression. Using this approach, the computer-optimized immunization strategy can increase cross-reactivity of the resulting anti-serum.

Many human vaccines require more than two immunizations to achieve adequate immunity. It is possible that a single prime-boost immunization strategy may not significantly raise CCD specific antibody levels. As an alternative strategy, the computer model disclosed herein can be used to test additional immunization regimens such as prime-boost-boost or prime-prime-boost-boost. Recent work has demonstrated that antibody levels to the influenza HA antigen plateau after repeated immunization, the computer model can be used to determine the number of immunizations needed to achieve maximum CCD specific antibody boosting.

Immunization with inert antigens often requires adjuvant. Qualene-based emulsion adjuvants have been shown to boost antibody levels in mice. For example, the ADDAVAX (INVIVOGEN) adjuvant can be used if recombinant G-protein alone is not sufficient to induce adequate antibody levels.

Example 3. CCD Specific Antibody Reduces Weight Loss and Virus Load after RSV Challenge An immunization strategy that increases levels of CCD specific antibody can also reduce weight loss and virus load in mice challenged with RSV. In addition, this immunity can be protective against strains from both subtypes. To test this, mice can be challenged with RSV after prime-boost immunization. Mice are first immunized with recombinant G-proteins and subsequently challenged with RSV. The mice can be prime-boost immunized with either the A2-B1 strain pair or the prime-boost pairs optimized in Example 2. Blood can be collected throughout the immunization process. Weight loss and viral load after viral challenge can be measured. Homologous prime-boost can be performed for comparison.

3.1 Immunization of Mice with Recombinant G-Protein.

Results from the computer model suggest that prime-boost immunization with A2 and B1 strains can result in boosting of CCD specific antibody levels. Both recombinant proteins and virus strains for both A2 and B1 strains were obtained (BEI Resources). Recombinant G-proteins to the computer-optimized strain pair can be created using the strategy outlined in Example 2. BALB/c mice can be prime-immunized with recombinant proteins from either A2 or B1 strains and subsequently boosted with homologous or heterologous antigens (10 mice per condition). In addition to this immunization, mice can be prime-boost immunized with recombinant proteins from the computer-optimized strain pair determined in Example 2. Serum can be collected and CCD specific antibody and total G-protein antibody can be measured by ELISA.

3.2 the Effect of Immunization Strategy on Viral Titer and Morbidity in Mice Challenged with RSV.

Figure 9:
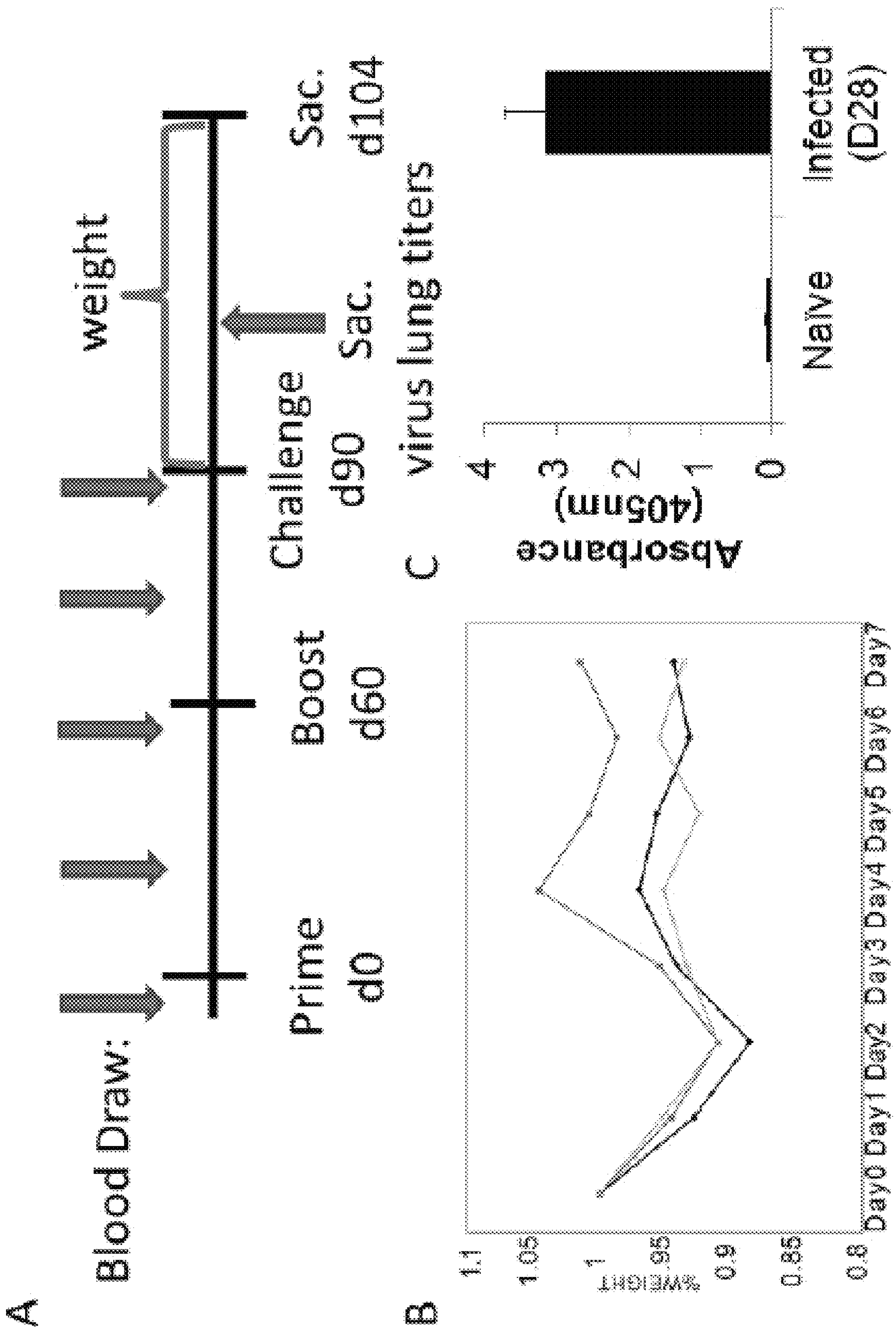
FIGS. 9A, 9B, and 9C show weight loss and seroconversion after infection with the RSV. (A) Experimental design of mice immunization and challenge experiments. (B) Weights of three 8-week old mice infected with the A2 RSV strain. (C) Total G-protein antibody levels 28 days after infection.
Figure 10:
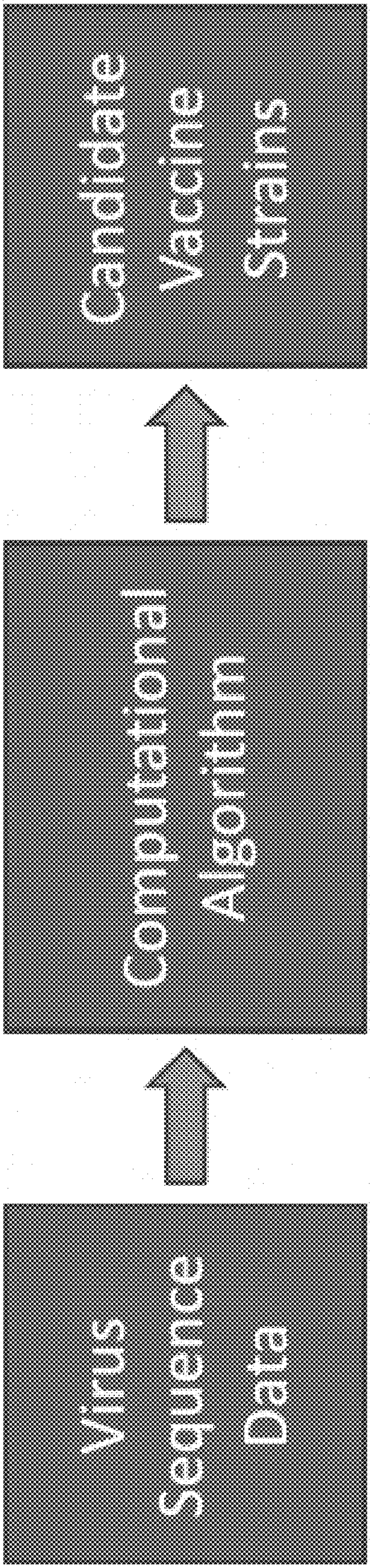
FIG. 10 shows an example of a method for selecting candidate vaccine strains.

In order to determine if boosting CCD specific antibody results in decreased RSV disease, mice were challenge with either A2 or B1 virus strains 60 days after boost immunization (FIG. 9A). Weight for each was measured daily for 14 days after infection to determine disease severity in the mice. Uninfected mice served as controls. A second set of mice were sacrificed 4 days post challenge and virus load in the lung determined. Inventor's group developed a method to determine virus load using real-time PCR. Using this method, mice lungs are homogenized and RNA extracted. Virus load can be determined by quantifying the viral RNA levels (RSM-M gene) in the mouse lung. Differences in weight loss and virus load between mice with different immunization strategies or infected with different RSV subtypes are statistically compared using ANOVA.

The results indicated a greater than 10% weight loss in BALB/C mice after challenged with RSV. Additional similar assays can be conducted using A129 interferon receptor knockout mice, which are highly susceptible to viral infection.

The CCD might turn out to be too broad of a vaccine target and perhaps antibodies need to be directed specifically at the CX3C region. In this case, mutations can be incorporated into the non-CX3C region of the CCD in order to dissuade the recall of memory B cells to this region during boosting and provide greater boosting to the CX3C region.

The uniqueness of the immune focusing strategy is that it can be used to focus the antibody response to any region of the virus. An alternative target would be neutralizing antigenic sites on the F protein, which has been implicated in both attachment to the host membrane as well as entry of the virus into the host cell. A strategy that induces both CCD specific and F protein specific antibodies could also be used.

Example 4. Computer-Optimized Immunization Strategy to Boost Highly Cross-Reactivity Antibodies to RSV Rational:

RSV has been classified into two subtypes, A and B, and multiple genetic clades based on genomic and antigenic properties of the surface proteins. RSV contains 3 surface proteins (G, F, and SH), with the G-protein most abundant on the surface. Genetic variability across strains is greatest in G-protein with the exception of a conserved region, the CCD. The CCD contains a CX3C chemokine receptor motif that facilitates the attachment of RSV to primary adult human epithelial cells. Immunization regimens that induce CCD specific antibodies can be highly cross-reactive and show increased neutralization efficacy.

Methods:

A computational model was developed to simulate humoral immune responses to influenza viral antigens using antigenic distance estimates from viral sequence data (Anderson et al. 2018 BMC Bioinformatics, Anderson et al. bioRxiv 346726). A similar strategy using publicly available G-protein sequence data was used to simulate antibody responses to the RSV G-protein antigen. CCD specific antibody levels and antibody cross-reactive towards 10 chosen strains were tracked during the simulation. The Pediatric Human Lung Epithelial (PHLE) cell model of pediatric airway epithelium was used for virus neutralization and flow cytometry assays.

Sequence Analysis:

1608 RSV G protein sequences were obtained from Virus Pathogen Database and Analysis Resource (ViPR). Sequences were aligned (MUSCLE) and pairwise amino acid differences between all strains determined. The dimensionality of the resulting distance matrix mas reduced using Principal Coordinate Analysis as similarly described (Anderson et al. BMC Bioinformatics 2018, Anderson et al. Scientific Reports 2018, Anderson et al. PLoS One 2016).

PHLE Cell Model:

Whole pediatric lungs were digested with a protease cocktail containing collagenase, dispase, elastase and DNAase. Primary pediatric Human Lung Epithelial (PHLE) cell cultures were expanded in a small airway growth medium (PROMOCEL1 C-21070). Fibroblasts were removed with gentle trypsinization. PHLE were grown as resistant monolayers on collagen I coated transwell plates, and differentiated at ALI for 14 days in a PNEUMACULT-ALI medium (STEMCELL 05021).

qRT-PCR:

RNA was isolated using the ABSOLUTELY RNA kit (AGILENT; Cat #400805) with DNAse treatment. cDNA synthesis was performed using an ISCRIPT cDNA synthesis kit (BIO-RAD 1708890) using SYBR green chemistry (APPLIED BIOSYSTEMS 4367659) on a VIIA7 (APPLIED BIOSYSTEMS).

RSV Infection:

Cells were infected by application of A2 RSV strain containing a GFP construct at MOI=1 in 500 μl on the apical surface for 2 hrs at 37° C. The cells were washed and returned to the incubator for up to 24 hours.

Flow Cytometry:

Following RSV infection, the cells were recovered by trypsinization, blocked with BSA, and incubated with anti-CX3CR1 antibody (ABCAM ab8021) for 1 hr at RT. Cells were analyzed for GFP and CX3CR1 on a BD LSRII. N=3.

RSV Blocking Using Anti-CX3CR1:

Indicated doses of anti-CX3CR1 (MBL-Cat #D070-3) were pre-incubated with cells for 1 hr at 37° C. prior to RSV infection. N=4.

RSV Blocking Using Recombinant CX3CR1:

Recombinant-CX3CR1 (0.6 μg/ml) was pre-incubated with RSV for 1 hr at 37° C. prior to infection. N=3.

Computer Simulations:

Gillespie-algorithm-based simulations were performed using an agent-based computational model of the humoral immune system. The model uses antigenic distances between G-proteins as input and uses a stochastic simulation approach to model the humoral immune response. The model tracts B cell and antibody abundance and specificity. The model is similar to the influenza model previously reported (Anderson et al. bioRxiv 346726). Error bars represent standard deviation of 50 simulations.

Statistics:

Groups were compared using two-tailed t-test using the R base package. Linear regression models (l.m.) were performed using the R base package.

Results:

Analysis of RSV genetic sequence data from 1608 strains ranging 60 years found that the CCD was most conserved (12% mean percent-amino-acid-difference) compared to the heparin-binding domain (HBD) and mucin-like domains 1 & 2 (22%, 31%, and 32%, respectively). The CX3C region was 100% conserved within subtypes. In vitro studies demonstrated that viral load was higher (1.9-fold) in CX3CR1 positive epithelial cells compared to CX3CR1 negative cells. Moreover, blocking the G-protein/CX3CR1 interaction lead to a significant reduction (2.3-fold) in viral load. In silico simulations using antigenic estimates of the G-protein suggest that heterologous prime-boost immunization with G-protein antigen from A2 and B1 strains may be used to boost CCD-specific antibody. It was found that this immunization strategy led to a 1.8-fold increase in CCD-specific antibody in silico. Moreover, the strategy increased antibody cross-reactivity towards 10 genetically distinct RSV strains.

Conclusion:

The computer simulations and in vitro work performed here support that an immunization strategy that induces CCD specific antibody would be both neutralizing and highly cross-reactive. The RSV G-protein is variable, both within and across subtypes, but contains a CCD. CX3CR1 positive cells are more susceptible to RSV infection and blocking the CX3C/CX3CR1 interaction reduces viral load in a pediatric airway model. Computer simulations suggest that heterologous prime-boost immunization can enhance CCD specific antibody and increase the cross-reactivity of the resulting antibody.

Example 5. Vaccine Formulations and Two-Part Immunization Regimen Prevented Weight-Loss in Mice after RSV Challenge In this example, vaccine formulations computer optimized in the manner described in Example 4 were tested in a murine challenge model to demonstrate physiological relevance of CX3CR1 and the potential for antibodies that bind to these regions to provide protection against RSV infection.

As described above, RSV circulates in the human population as two genetically distinct subtypes (A and B), with both subtypes co-circulating each year. Although a subtype may dominate consecutive years, the representative strain is unique each year. Therefore, an RSV vaccine must provide protection against both subtypes and be robust to these genetic changes.

Although genetic difference can be found among all viral proteins, the greatest genomic variation occurs in the G-protein. Antibodies that bind this region can disrupt attachment of the virus to the host cell resulting in an unsuccessful infection. Unlike other regions, the inner-loop of the G-protein, the CCD, is highly conserved. Induction of antibodies to the CCD region have been shown to be cross-reactive to both A and B RSV subtypes. Induction of antibodies cross-reactive to this functional, highly conserved domain of RSV have been shown to reduce RSV disease. Taken together, CCD is a prime target for an RSV vaccine.

In addition to conservation, the CCD is a highly functional region of the virus. The CCD region has been shown to bind the fractalkine receptor (CX3CR1) on human lung epithelial cells facilitating the attachment of the virus to the host and alter cellular transcription and cytokine levels of host cells. The secreted form of the G-protein has also been shown to modulate immune cells during RSV infection. Given both the conservation and the functional significance of the CCD domain, enhancing antibody responses to this region may provide the neutralizing efficacy and cross-reactivity needed for an effective universal RSV vaccine.

Two vaccine formulations were made for a two-part immunization regimen. The vaccine formulation for Part 1 contained (i) 5 micrograms recombinant RSV A2 strain G-protein in 25 microliters phosphate buffered saline and (ii) 25 microliters squalene-based oil-in-water nano-emulsion adjuvant. The vaccine formulation for Part 2 contained (i) 5 micrograms recombinant RSV B1 strain G-protein in 25 microliters phosphate buffered saline and (ii) 25 microliters squalene-based oil-in-water nano-emulsion adjuvant.

To immunize mice with this regimen, vaccine formulation Part 1 was injected into the posterior thigh muscle of 6-8 week old BALB/c mice (priming). Six weeks later, the Part 2 vaccine formulation was injected into the same muscle (boosting). The mice were then challenged with RSV A2-19F virus. Briefly, 10 mice were used in total. Five mice were challenged 30 days after immunized with Part 2 of the vaccine formulation. The other five mice served as controls and were unimmunized and challenged with the A2-19F strain. Weights of the mice were taken over the 12 days and mice were sacrificed subsequently.

Lung and blood samples were taken from each mouse at day 12 post challenge. Blood was taken by tail vein bleed. The left lung lobe was taken for RNA isolation. RSV-M transcript levels was measured by real-time qPCR. Serum antibody levels were determined by ELISA.

The results indicated that mice immunized with the vaccine formulations and challenged 28 days post immunization with RSV A2-19F strain demonstrated increased G-protein specific antibody prior to challenge (FIG. 17A). Moreover, antibody levels were increased post-challenge demonstrating increased immunity both prior and during RSV infection (FIG. 17A). Mice immunized with the computer optimized vaccine formulations had little weight-loss while naïve mice shown a significant loss in weight after RSV challenge (FIG. 17B). Importantly, virus titers in the lung were undetectable after challenge in the immunized group (FIG. 17C).

The above results demonstrated that the vaccine formulations and two-part immunization regimen prevented weight-loss, a sensitive measure of disease severity of mice, after RSV challenge. Moreover, virus could not be detect in the lungs after infection in the vaccinated group, suggesting that the vaccine formulation induced sterilizing immunity The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A method of inducing an immune response in a subject, comprising (1) administering to the subject an effective amount of a prime immunogenic composition comprising a first recombinant RSV G-protein or an immunogenic fragment thereof; and then (2) administering to the subject an effective amount of a boost immunogenic composition comprising a second recombinant RSV G-protein or an immunogenic fragment thereof, wherein the first RSV G-protein or immunogenic fragment thereof is different from the second RSV G-protein or immunogenic fragment thereof and wherein one of the first RSV G-protein and the second RSV G-protein is from A2 strain and the other is from B1 strain.

2. The method of claim 1, wherein the first RSV G-protein is from A2 strain and comprises the sequence of SEQ ID NO: 1.

3. The method of claim 2, wherein the second RSV G-protein is from B1 strain and comprises the sequence of SEQ ID NO: 2.

4. The method of claim 1, wherein the first RSV G-protein is from B1 strain and comprises the sequence of SEQ ID NO: 2.

5. The method of claim 4, wherein the second RSV G-protein is from A2 strain and comprises the sequence of SEQ ID NO: 1.

6. The method of claim 1, wherein the prime immunogenic composition or the boost immunogenic composition, or both, comprise an adjuvant.

7. The method of claim 6, wherein the adjuvant comprises a squalene-based oil-in-water nano-emulsion.

8. The method of claim 6, wherein the w/v ratio of the RSV G-protein or the immunogenic fragment to the adjuvant ranges from about 1/1 to about 1/20.

9. The method of claim 6, wherein the w/v ratio of the RSV G-protein or the immunogenic fragment to the adjuvant is about 5 micrograms to about 25 microliters per dosage unit.

10. The method of claim 6, the time interval between administration of the first prime immunogenic composition and administration of the boost immunogenic composition is about 1 to about 24 months.

11. The method of claim 10, the time interval is about 6 months.

12. The method of claim 1, wherein the immunogenic fragment comprises one selected from the group consisted of SEQ ID Nos: 3-23.

13. The method of claim 1, wherein the immunogenic fragment comprises a central conserved-domain (CCD).

14. The method of claim 1, wherein the subject is a human.

* * * * *